United States Patent
Barmes et al.

(10) Patent No.: US 11,779,381 B2
(45) Date of Patent: Oct. 10, 2023

(54) BONE FIXATION SYSTEM, ASSEMBLY, IMPLANTS, DEVICES, ALIGNMENT GUIDES, AND METHODS OF USE

(71) Applicant: Paragon 28, Inc., Englewood, CO (US)

(72) Inventors: Frank Barmes, Parker, CO (US); Spanky Raymond, Uniontown, OH (US); Joseph Dogué, Aurora, CO (US); Albert Dacosta, Lone Tree, CO (US); Matt Jarboe, Ada, MI (US)

(73) Assignee: PARAGON 28, INC., Englewood, CO (US)

( * ) Notice: Subject to any disclaimer, the term of this patent is extended or adjusted under 35 U.S.C. 154(b) by 98 days.

(21) Appl. No.: 17/248,980

(22) Filed: Feb. 16, 2021

(65) Prior Publication Data

US 2021/0161575 A1 Jun. 3, 2021

Related U.S. Application Data

(60) Division of application No. 15/942,040, filed on Mar. 30, 2018, now Pat. No. 10,918,431, which is a
(Continued)

(51) Int. Cl.
*A61B 17/17* (2006.01)
*A61B 17/80* (2006.01)
(Continued)

(52) U.S. Cl.
CPC ...... *A61B 17/8897* (2013.01); *A61B 17/1717* (2013.01); *A61B 17/1775* (2016.11);
(Continued)

(58) Field of Classification Search
CPC ............ A61B 17/7059; A61B 17/8033; A61B 17/8047; A61B 17/8052; A61B 17/8057
See application file for complete search history.

(56) References Cited

U.S. PATENT DOCUMENTS

| 5,429,641 A | 7/1995 | Gotfried |
| 6,342,057 B1 | 1/2002 | Brace |

(Continued)

FOREIGN PATENT DOCUMENTS

| EP | 0617927 | 10/1994 |
| EP | 1273271 | 8/2007 |

(Continued)

OTHER PUBLICATIONS

Budny et al. "Naviculocuneiform Arthrodesis," Clinics in Podiatric Medicine and Surgery, vol. 24, pp. 753-763, Oct. 2007.
(Continued)

*Primary Examiner* — Nicholas W Woodall
(74) *Attorney, Agent, or Firm* — Heslin Rothenberg Farley & Mesiti P.C.; Jacquelyn A. Graff, Esq.

(57) ABSTRACT

Implants, guides, devices, instruments, systems and methods for fixing a joint using bone plates are disclosed. The bone fixation system includes an alignment guide with a first end and a second end, an alignment wire rotatably coupled to the first end of the alignment guide, and a coupling member slidingly engaging a first portion of the alignment guide near the first end. The plate includes a body including a first end and a second end, a plurality of lobes extending from the body, a plurality of screw holes extending through the body and each screw hole of the plurality of screw holes positioned in a lobe of the plurality of lobes, and an alignment hole positioned along a longitudinal axis of the body. A method of using a bone fixation system for fixation of at least two bones is also disclosed.

16 Claims, 36 Drawing Sheets

Related U.S. Application Data continuation of application No. PCT/US2018/025443, filed on Mar. 30, 2018.

(60) Provisional application No. 62/478,984, filed on Mar. 30, 2017.

(51) Int. Cl.
  *A61B 17/88* (2006.01)
  *A61B 17/00* (2006.01)
  *A61B 17/68* (2006.01)

(52) U.S. Cl.
  CPC ...... *A61B 17/8057* (2013.01); *A61B 17/8061* (2013.01); *A61B 17/1728* (2013.01); *A61B 2017/00477* (2013.01); *A61B 2017/681* (2013.01)

(56) References Cited

U.S. PATENT DOCUMENTS

| | | | |
|---|---|---|---|
| 6,692,496 | B1 | 2/2004 | Wardlaw |
| 7,011,665 | B2 | 3/2006 | Null |
| 7,316,687 | B2 | 1/2008 | Aikins |
| 8,231,627 | B2 | 7/2012 | Huebner |
| 8,535,355 | B2 | 9/2013 | Prasad |
| 9,161,796 | B2 | 10/2015 | Chiodo |
| 9,421,103 | B2 | 8/2016 | Jeng et al. |
| 10,327,829 | B2 | 6/2019 | Dacosta et al. |
| 2004/0102776 | A1 | 5/2004 | Huebner |
| 2004/0102777 | A1 | 5/2004 | Huebner |
| 2004/0193165 | A1 | 9/2004 | Orbay |
| 2005/0027296 | A1* | 2/2005 | Thramann ............... A61B 17/92 606/287 |
| 2005/0216008 | A1* | 9/2005 | Zwirnmann ............ A61B 17/68 606/915 |
| 2006/0189996 | A1 | 8/2006 | Orbay |
| 2007/0173843 | A1* | 7/2007 | Matityahu ............... A61B 17/80 606/281 |
| 2007/0239168 | A1 | 10/2007 | Kuenzi |
| 2007/0270850 | A1 | 11/2007 | Geissler |
| 2008/0015590 | A1 | 1/2008 | Sanders |
| 2008/0091197 | A1 | 4/2008 | Coughlin |
| 2008/0188852 | A1 | 8/2008 | Matityahu |
| 2009/0036931 | A1 | 2/2009 | Pech |
| 2009/0088767 | A1 | 4/2009 | Leyden |
| 2009/0093849 | A1 | 4/2009 | Grabowski |
| 2009/0171398 | A1* | 7/2009 | Phillips ............... A61B 17/8061 606/280 |
| 2010/0179597 | A1 | 7/2010 | Henderson |
| 2011/0046681 | A1 | 2/2011 | Prandi et al. |
| 2011/0144647 | A1 | 6/2011 | Appenzeller |
| 2011/0144700 | A1 | 6/2011 | Konieczynski |
| 2011/0218576 | A1 | 9/2011 | Galm |
| 2011/0224734 | A1 | 9/2011 | Schelling |
| 2011/0264149 | A1 | 10/2011 | Pappalardo |
| 2011/0270319 | A1 | 11/2011 | Sheffer |
| 2012/0078252 | A1 | 3/2012 | Huebner |
| 2012/0316562 | A1 | 12/2012 | Costa |
| 2013/0018424 | A1* | 1/2013 | Subik ............... A61B 17/8085 606/281 |
| 2013/0046311 | A1 | 2/2013 | Blake et al. |
| 2013/0150903 | A1 | 6/2013 | Vincent |
| 2013/0172942 | A1 | 7/2013 | Lewis et al. |
| 2014/0066996 | A1 | 3/2014 | Price et al. |
| 2014/0107798 | A1 | 4/2014 | Jeng et al. |
| 2014/0180348 | A1 | 6/2014 | Thoren et al. |
| 2015/0032168 | A1 | 1/2015 | Orsak et al. |
| 2015/0182267 | A1 | 7/2015 | Wolf et al. |
| 2015/0359580 | A1 | 12/2015 | Dacosta et al. |
| 2016/0030064 | A1 | 2/2016 | DaCosta et al. |
| 2016/0135858 | A1 | 5/2016 | Dacosta et al. |
| 2016/0310191 | A1 | 10/2016 | Seykora et al. |
| 2016/0324552 | A1 | 11/2016 | Baker et al. |
| 2016/0354128 | A1 | 12/2016 | Jeng |
| 2017/0056031 | A1 | 3/2017 | Awtrey et al. |
| 2018/0110530 | A1 | 4/2018 | Wagner et al. |
| 2018/0242988 | A1 | 8/2018 | Dacosta et al. |
| 2019/0015140 | A1 | 1/2019 | Dacosta et al. |

FOREIGN PATENT DOCUMENTS

| | | |
|---|---|---|
| EP | 2745786 | 6/2014 |
| EP | 3023068 | 5/2016 |
| FR | 3030221 | 6/2016 |
| JP | 04250156 | 9/1992 |
| WO | 2005089660 | 9/2005 |
| WO | 2012103335 | 8/2012 |
| WO | 2013009574 | 1/2013 |
| WO | 2014105750 | 7/2014 |
| WO | 2015094409 | 6/2015 |
| WO | 2015138542 | 9/2015 |
| WO | 2017004221 | 1/2017 |
| WO | 2017011656 | 1/2017 |
| WO | 2018157170 | 8/2018 |

OTHER PUBLICATIONS

Partial Supplementary European Search Report issued in European Patent Application No. 18757770.5 dated Dec. 3, 2020, 11 pages.
Partial Supplementary European Search Report issued in European Patent Application No. 18758239.0, dated Dec. 10, 2020, 11 pages.
European Communication Pursuant to Article 94(3) EPC (Office Action) for EP Application No. 18201132.0 dated Feb. 12, 2021, 5 pages.
Partial Supplementary European Search Report issued in European Patent Application No. 18777784.2, dated Jan. 14, 2021, 13 pages.
Extended European Search Report issued in European Patent Application No. 18757770.5, dated Mar. 9, 2021, 10 pages.
Extended European Search Report issued in European Patent Application No. 18758239.0, dated Apr. 8, 2021, 12 pages.
Extended European Search Report issued in European Patent Application No. 18831633.5, dated Apr. 16, 2021, 10 pages.
Extended European Search Report issued in European Patent Application No. 18777784.2, dated Apr. 16, 2021, 11 pages.

\* cited by examiner

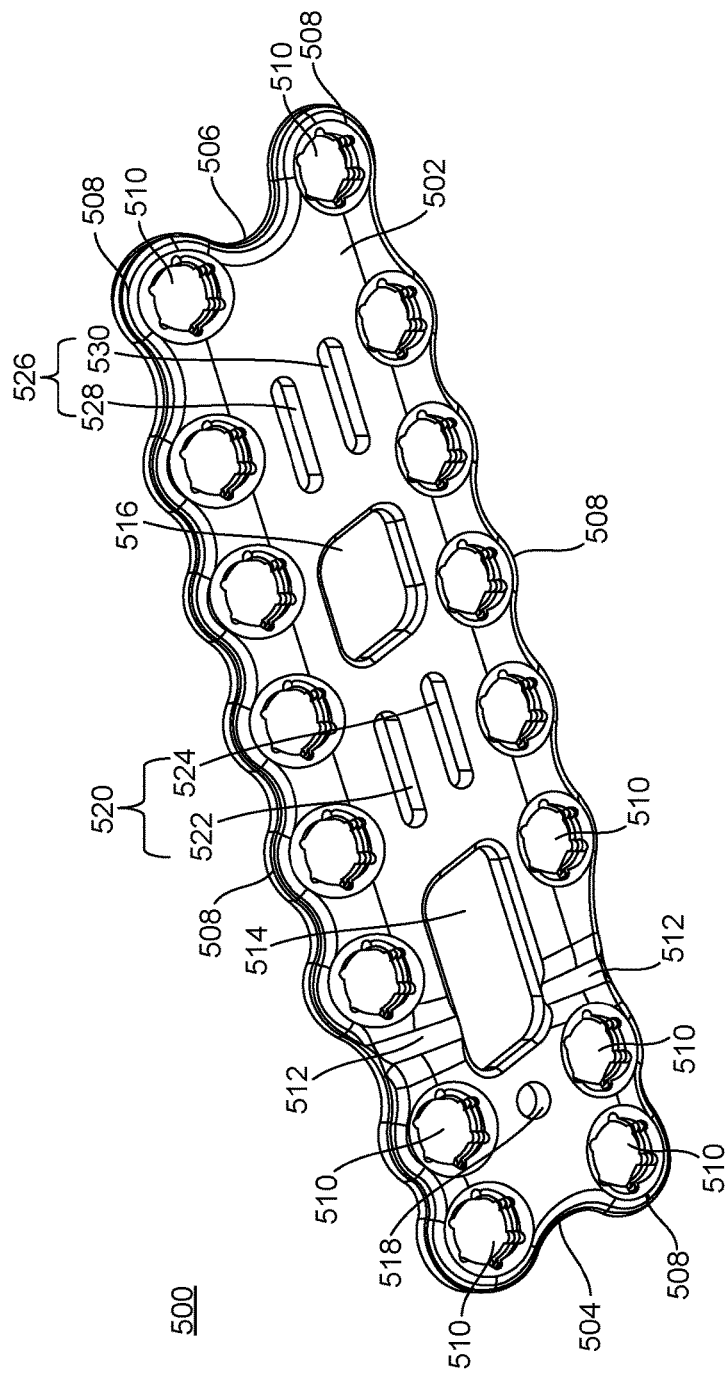
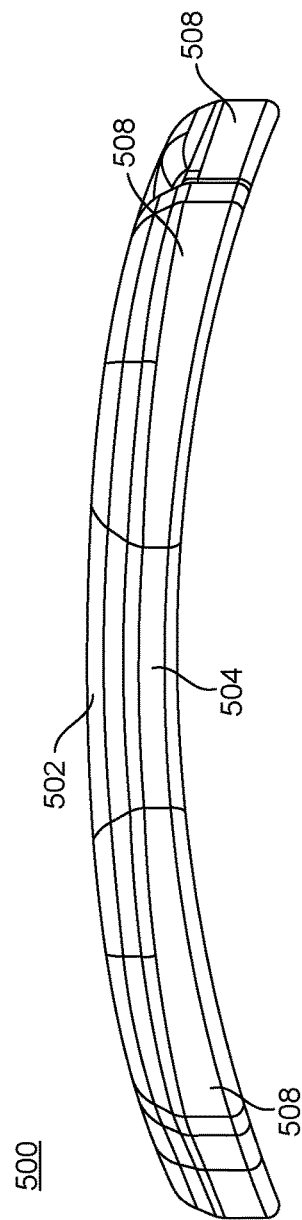
FIG. 38
FIG. 39

BONE FIXATION SYSTEM, ASSEMBLY, IMPLANTS, DEVICES, ALIGNMENT GUIDES, AND METHODS OF USE

CROSS REFERENCE TO RELATED APPLICATION

This application is a divisional of U.S. application Ser. No. 15/942,040 filed on Mar. 30, 2018, which will issue as U.S. Pat. No. 10,918,431 on Feb. 16, 2021, which is a continuation of PCT Application No. PCT/US2018/025443 filed on Mar. 30, 2018, and which claims priority benefit under 35 U.S.C. § 119(e) of U.S. provisional application No. 62/478,984 filed Mar. 30, 2017, which are incorporated herein by reference in their entireties.

TECHNICAL FIELD

The present disclosure relates generally to general, podiatric, and orthopaedic surgery related to fixation of prepared joint surfaces. More specifically, but not exclusively, the present disclosure relates to implants, guides, devices, instruments, systems and methods for fixing a joint using bone plates.

BACKGROUND OF THE INVENTION

In patients with Charcot neuroarthropathy and other deformities of the foot there may be a breakdown of the arch of the foot including the medial column resulting in pain, areas of increased pressure resulting in ulceration and instability. In order to alleviate the pain, increased pressure and instability, it is sometimes necessary to perform arthrodesis or fusion on the bones of the foot and ankle to place the foot back into a plantigrade position. New and improved bone fixation systems, assemblies, implants, alignment guides, and methods are needed to improve the stability of the patient's foot after arthrodesis or fusion.

SUMMARY OF THE INVENTION

The present disclosure is directed toward devices and methods for use in fixation of a patient's joints or for fixation of a fracture. The alignment guides provide an orientation for securement of a beaming screw and bone plates across a patient's joint or fracture.

In one aspect of the present disclosure provided herein, is a bone fixation system. The bone fixation system includes an alignment guide with a first end and a second end, an alignment wire rotatably coupled to the first end of the alignment guide, and a coupling member slidingly engaging a first portion of the alignment guide near the first end.

In another aspect of the present disclosure provided herein, is a bone plate, that includes a body with a first end and a second end, a plurality of lobes extending from the body, a plurality of screw holes extending through the body with each screw hole of the plurality of screw holes being positioned in at least one lobe of the plurality of lobes, and an alignment hole positioned along a longitudinal axis of the body.

In yet another aspect of the present disclosure provided herein, is a method of using a bone fixation system for fixation of at least two bones. The method includes creating an incision near the at least two bones and preparing the at least two bones for fixation. The method also includes inserting an alignment wire into one of the at least two bones and coupling an alignment guide to the alignment wire. The method further includes positioning a bone plate on the at least two bones and inserting a beaming screw into the at least two bones. Finally, the method includes securing the bone plate to the at least two bones and closing the incision.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

FIG. 38 is a top perspective view of the bone plate of FIG. 27, in accordance with an aspect of the present disclosure;

FIG. 39 is an end view of the bone plate of FIG. 27, in accordance with an aspect of the present disclosure;

DETAILED DESCRIPTION FOR CARRYING OUT THE INVENTION

Figure 1:
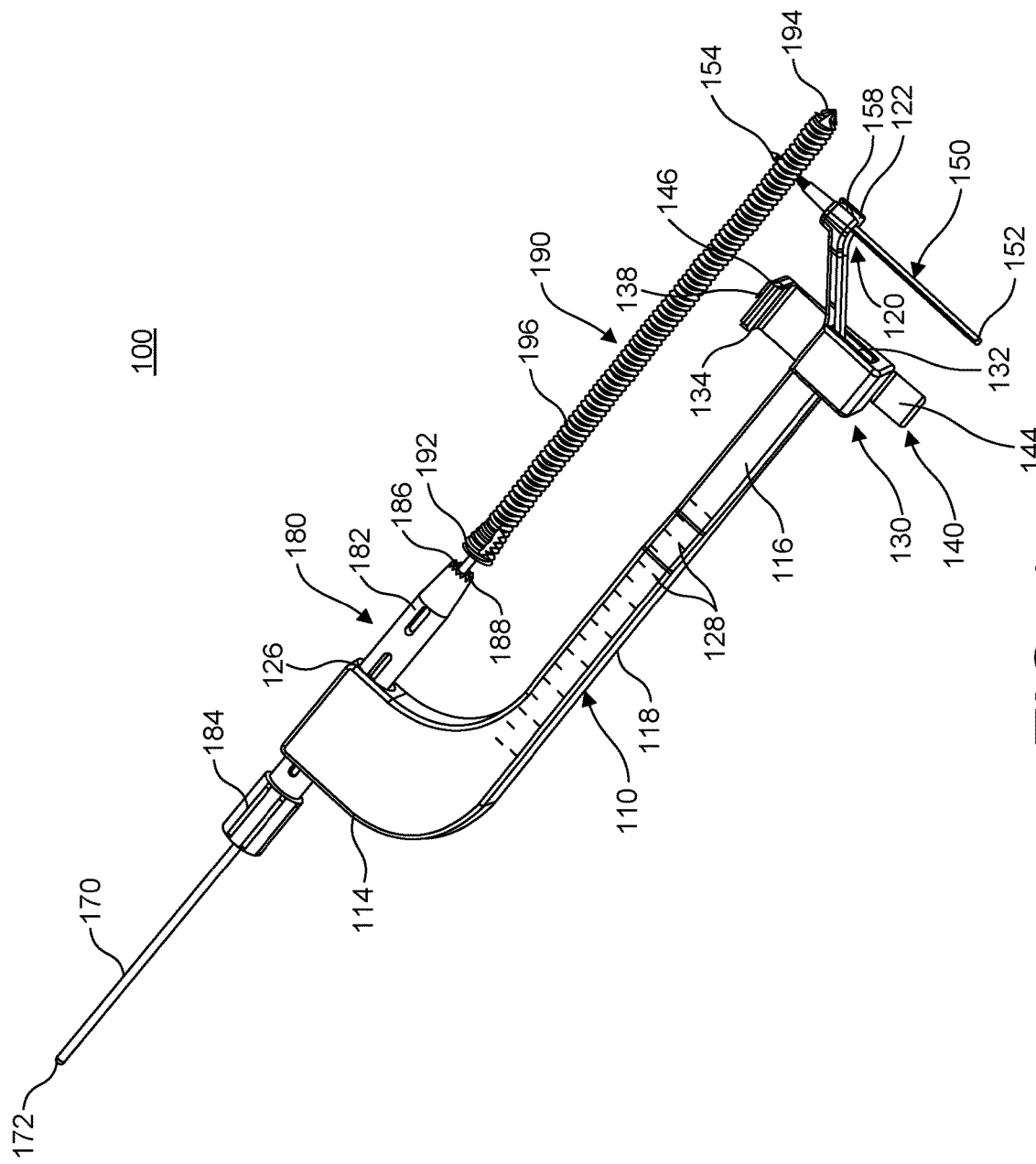
FIG. 1 is a top perspective view of one embodiment of a bone fixation system, in accordance with an aspect of the present disclosure.
Figure 2:
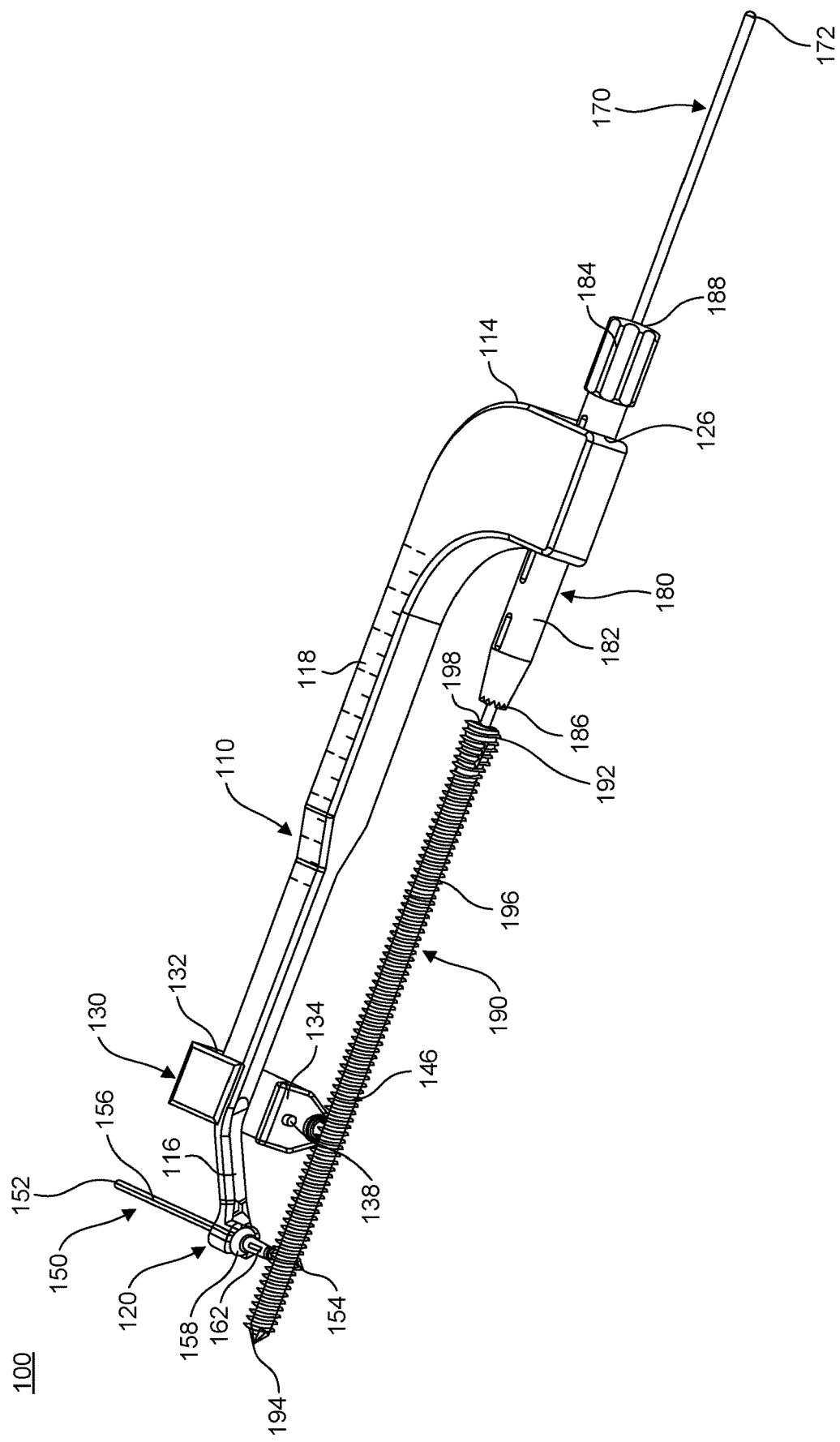
FIG. 2 is a first side perspective view of the bone fixation system of FIG. 1, in accordance with an aspect of the present disclosure.
Figure 3:
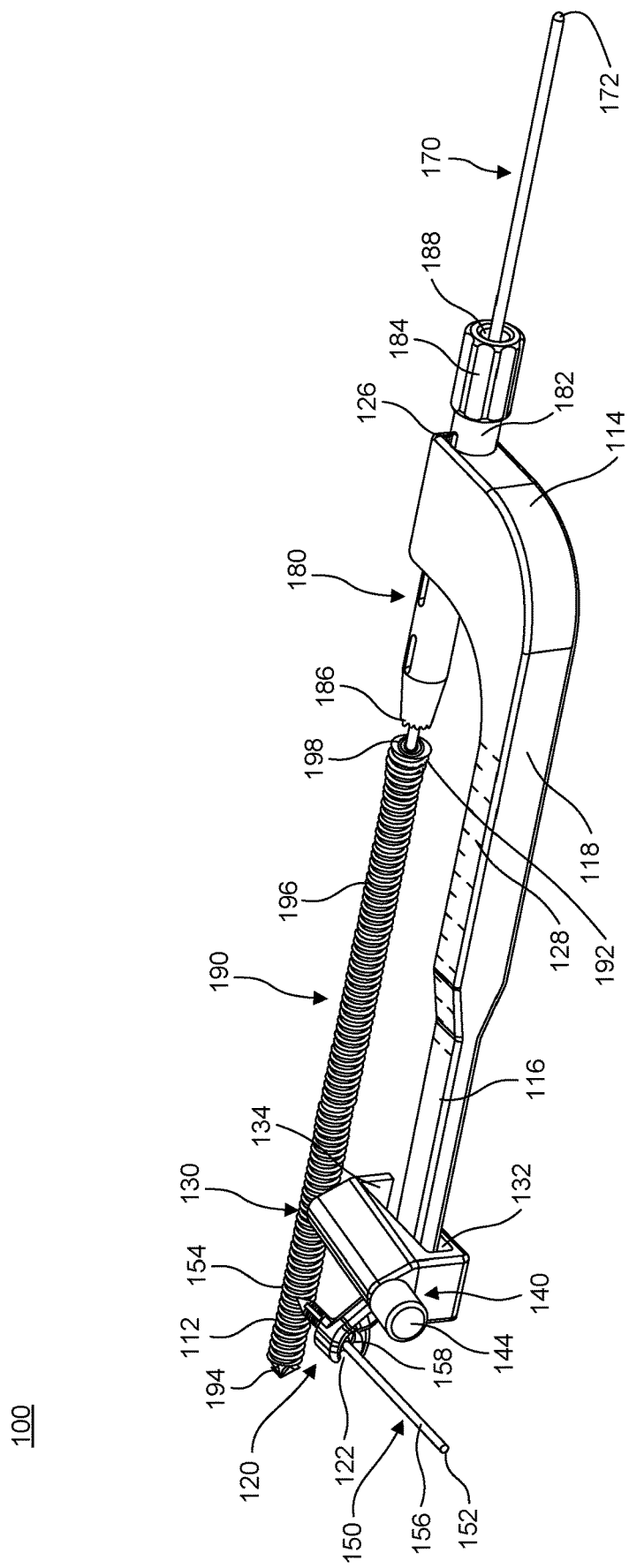
FIG. 3 is a second side perspective view of the bone fixation system of FIG. 1, in accordance with an aspect of the present disclosure.
Figure 4:
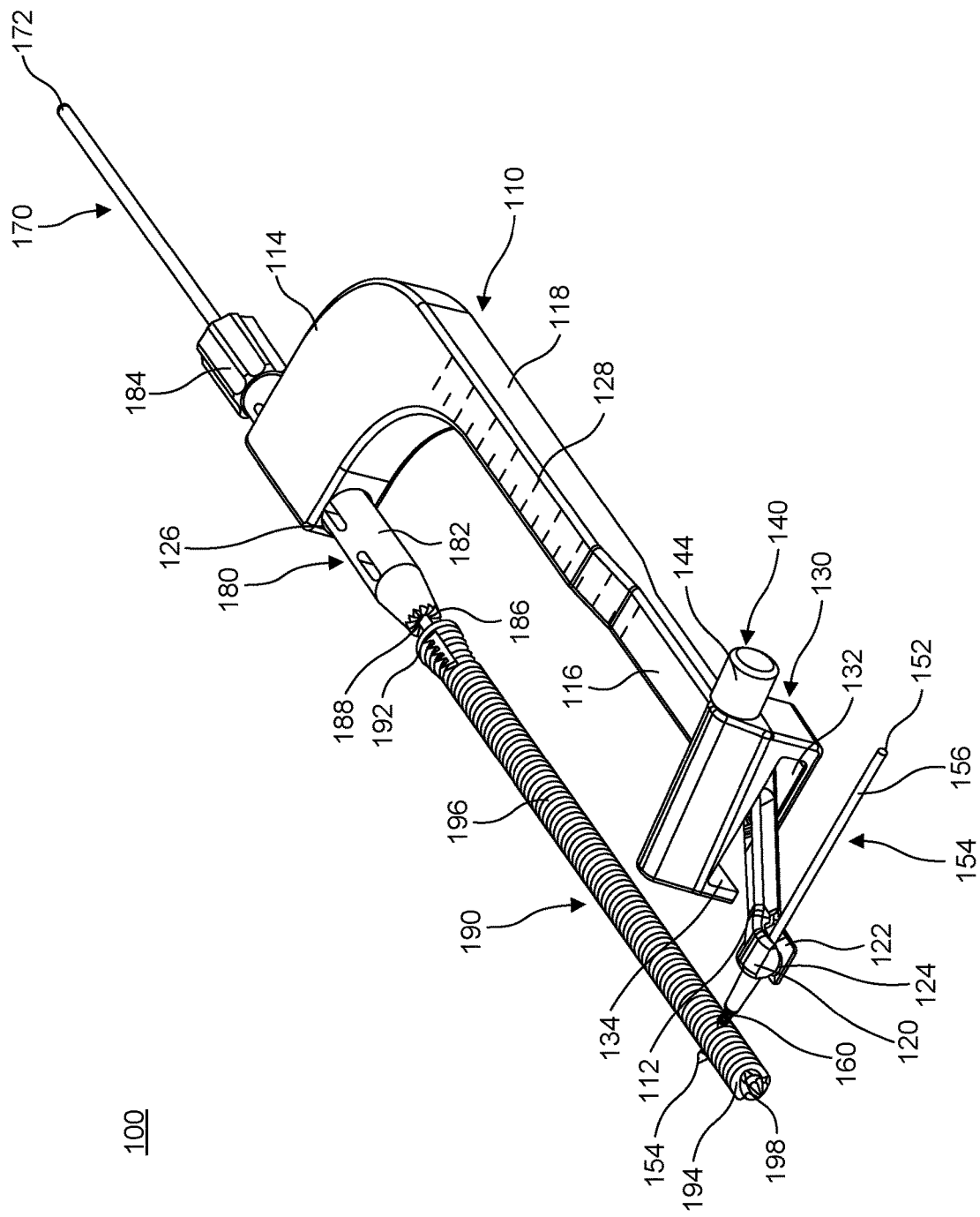
FIG. 4 is a first end perspective view of the bone fixation system of FIG. 1, in accordance with an aspect of the present disclosure.
Figure 5:
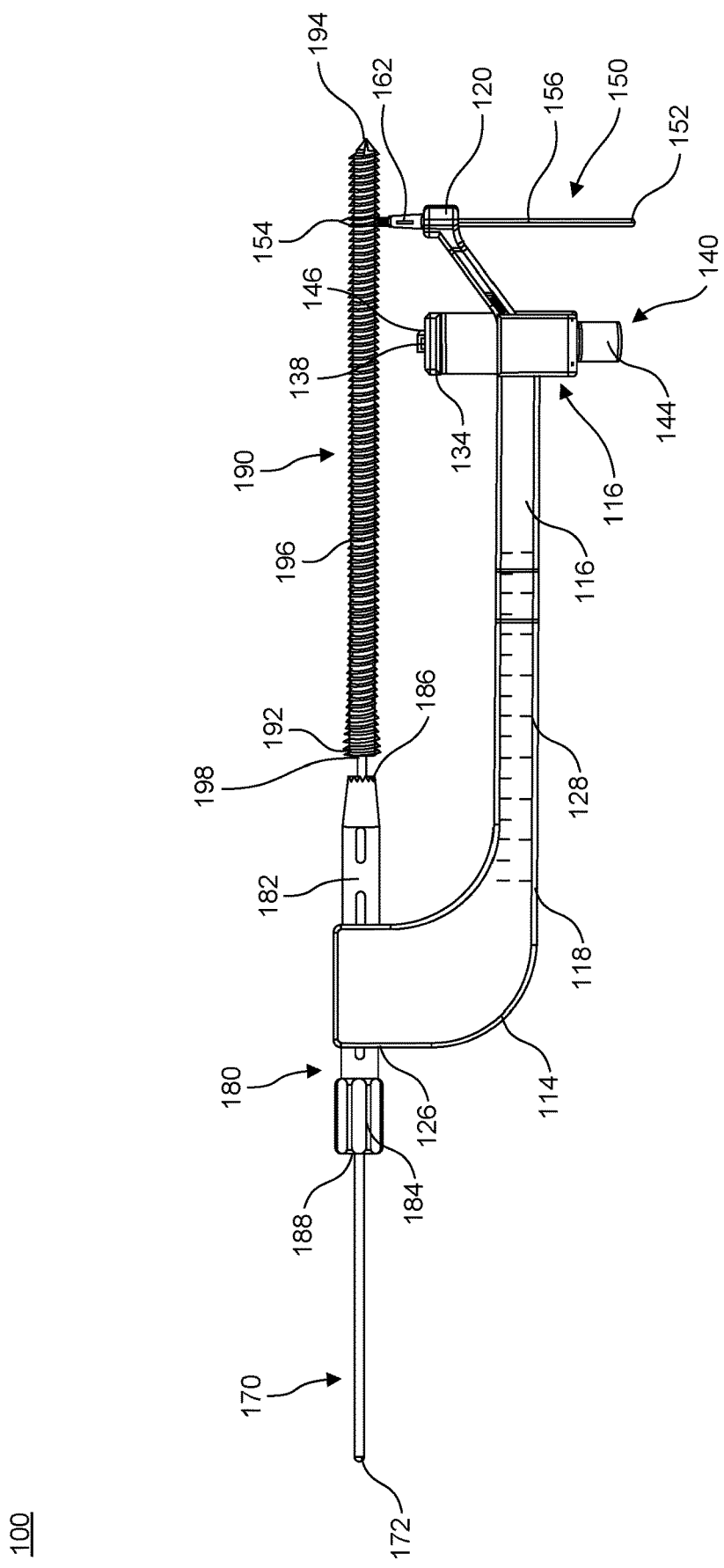
FIG. 5 is a top view of the bone fixation system of FIG. 1, in accordance with an aspect of the present disclosure.

Generally stated, disclosed herein are implants, guides, devices, instruments, and systems for fixing a joint using bone plates. Further, methods for using the implants, guides, devices, instruments and systems are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation and methods are described herein with reference to use with the bones of the foot, the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the implants, devices, instrumentation and methods, and the aspects, components, features and the like thereof, described herein with respect to the right foot may be mirrored so that they likewise function with the left foot. Further, the implants, devices, instrumentation and methods, and the aspects, components, features and the like thereof, disclosed herein are described with respect to the foot for brevity purposes, but it should be understood that the implants, devices, instrumentation and methods may be used with other bones of the body having similar structures.

Referring to the drawings, wherein like reference numerals are used to indicate like or analogous components throughout the several views, and with particular reference to FIGS. 1-10, there is illustrated an exemplary embodiment of a bone fixation system 100 including a targeting guide assembly and a bone plate 200, 250. The bone fixation system 100 includes an arm or alignment guide 110, a plate attachment member 130, a set screw or plate attachment member 140, a guide wire or sphere wire 150, a guide wire or k-wire 170, a guide wire sleeve 180, and a screw 190.

As shown in FIGS. 6-10, the alignment guide 110 includes a first end 112 and a second end 114. The first end 112 includes a first portion or base 116 and the second end 114 includes a second portion 118. The second portion 118 may have a width, for example, greater than the first portion 116 or the same width across its entire length. The alignment guide 110 may taper from the second portion 118 to the first portion 116. The first portion 116 may also include a pivoting head member 120 at the first end 112. The pivoting member 120 may include a channel 122 forming an opening in the pivoting head member 120. The channel or opening 122 may allow for the pivoting member 120 to deform or deflect for insertion of the sphere wire 150. The channel or opening 122 may also provide a recess for the first end 152 of the sphere wire 150 while the pivoting member 120 is pivoting on the pivot protrusion 158 of the sphere wire 150. The channel 122 may include two retaining members or recesses 124 on an interior surface of the pivoting member 120. Alternatively, the channel 122 may include a plurality of deformable retaining members (not shown) separated by a plurality of recesses that surround the channel 122 and are sized and shaped to receive the pivot protrusion 152. The second portion 118 may include an opening or through hole 126 extending through the second end 114 of the alignment guide 110. The alignment guide 110 may also include length or measurement indicator lines 128 positioned along the region between the first and second portions 116, 118 and along the second portion 118.

The plate attachment or coupling member 130 may include a channel 132 extending through the coupling member 130, as shown in FIGS. 6-10. The channel 132 may be, for example, sized and shaped to slide over the first portion 116 of the alignment guide 110. The coupling member 130 may also include a leg or extension member 134 extending out at a bottom of the coupling member 130. In addition, the coupling member 130 may include an opening 136 extending through the coupling member 130 along a longitudinal axis. The extension member 134 may include an alignment protrusion 138 extending from a bottom of the extension member 134, as shown in FIGS. 2, 5, 8 and 10. The alignment protrusion 138 may be sized and shaped to engage a bone plate, for example, bone plate 200.

With continued reference to FIGS. 6-10, the set screw or plate attachment member 140 includes a body 142 with a first end and a second end. The set screw 140 may also include a head portion 144 at the first end and a threaded portion 146 at the second end. The head portion 144 may have a diameter larger than a diameter of the body 142. The diameter of the head portion 144 may also be larger than the diameter of the opening 136 in the coupling member 130. The threaded portion 146 of the set screw 140 may include a thread that corresponds to the threading in an opening or screw hole of the bone plate 200.

The sphere wire 150 may include a first end 152 and a second end 154, as shown in FIGS. 1-10. The terms "sphere wire," "pivoting member," "grip wire," and "alignment wire" may be used interchangeably herein as the each essentially refer to a wire including a protrusion. The sphere wire 150 may also include a wire portion 156 extending from the first end 152 to a pivot protrusion or spherical member 158. The pivot protrusion 158 may be, for example, spherical or may have a circular or round cross-section and be sized and shaped to match the retaining member or recesses 124 in the pivoting head member 120 at the first end 112 of the alignment arm 110. The pivot protrusion 158 may rotate within the retaining member 124 in the pivoting head 120. The pivoting member 150 may also include a threaded insertion end 160 and a tapered region 162 extending between the pivot protrusion 158 and the insertion end 154. The insertion end 154 may have a pointed tip for insertion into the patient's foot.

Figure 6:
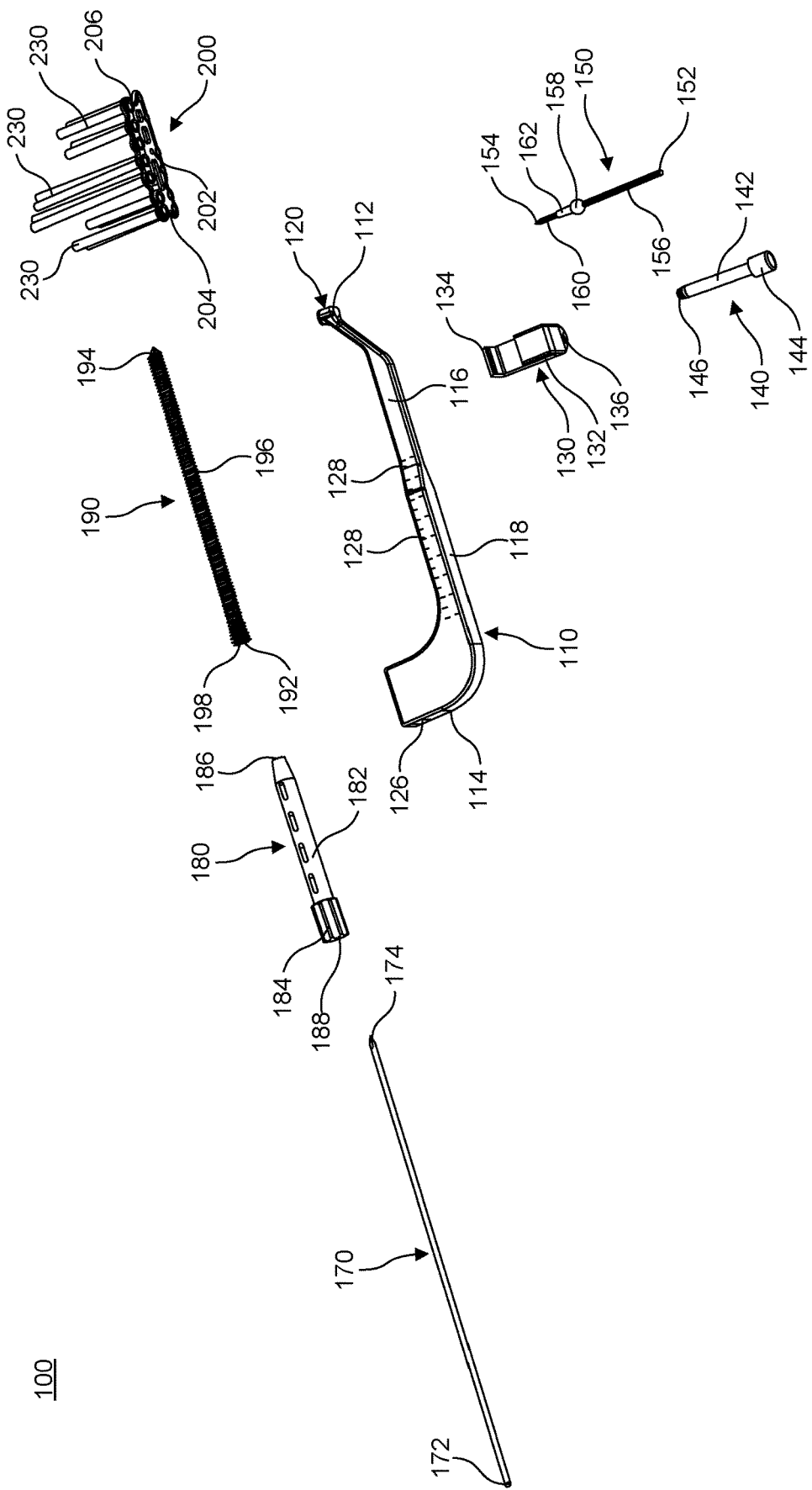
FIG. 6 is an exploded, top perspective view of the bone fixation system of FIG. 1 and a bone plate and fasteners, in accordance with an aspect of the present disclosure.
Figure 7:
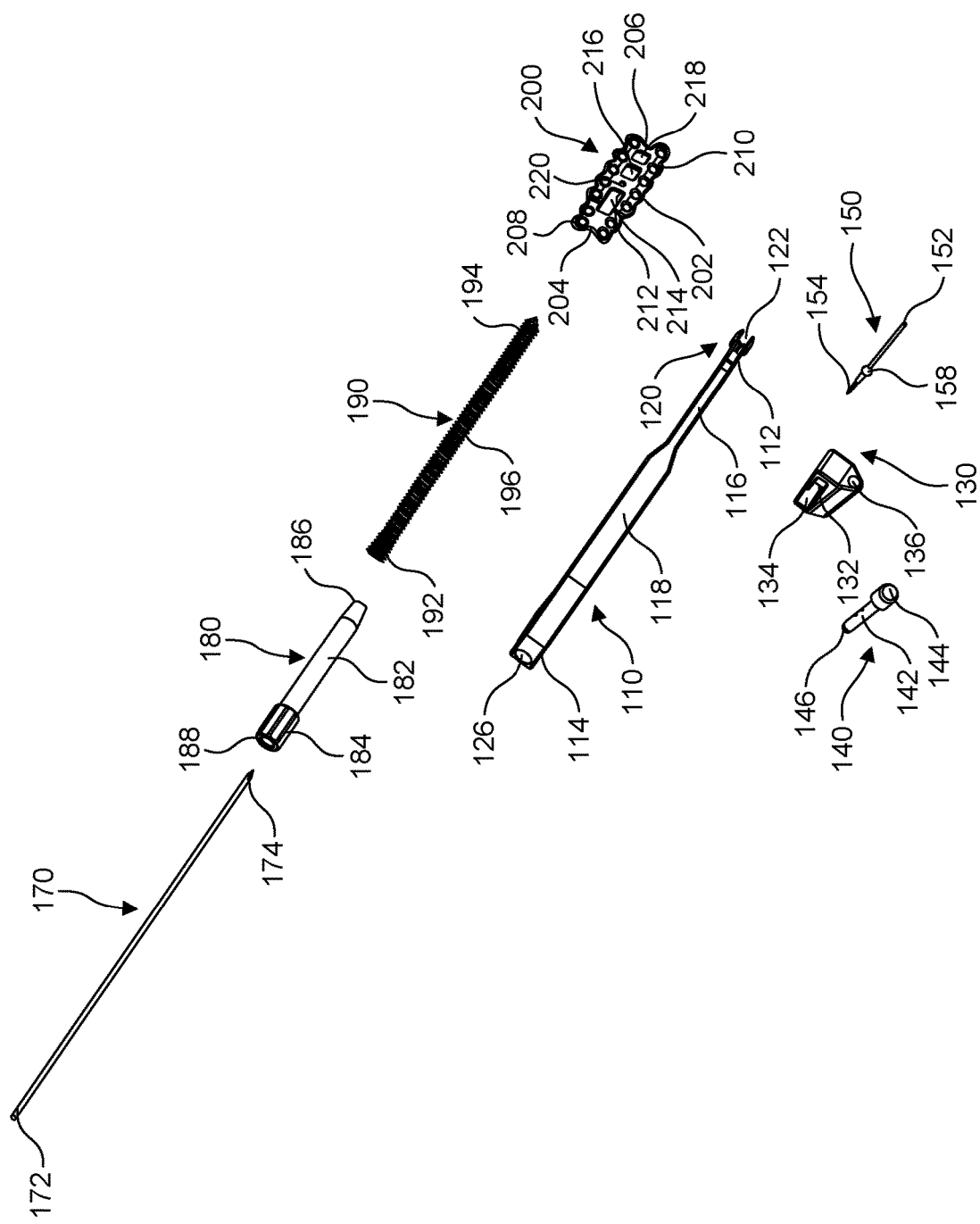
FIG. 7 is an exploded, side view of the bone fixation system and bone plate of FIG. 6, in accordance with an aspect of the present disclosure.
Figure 8:
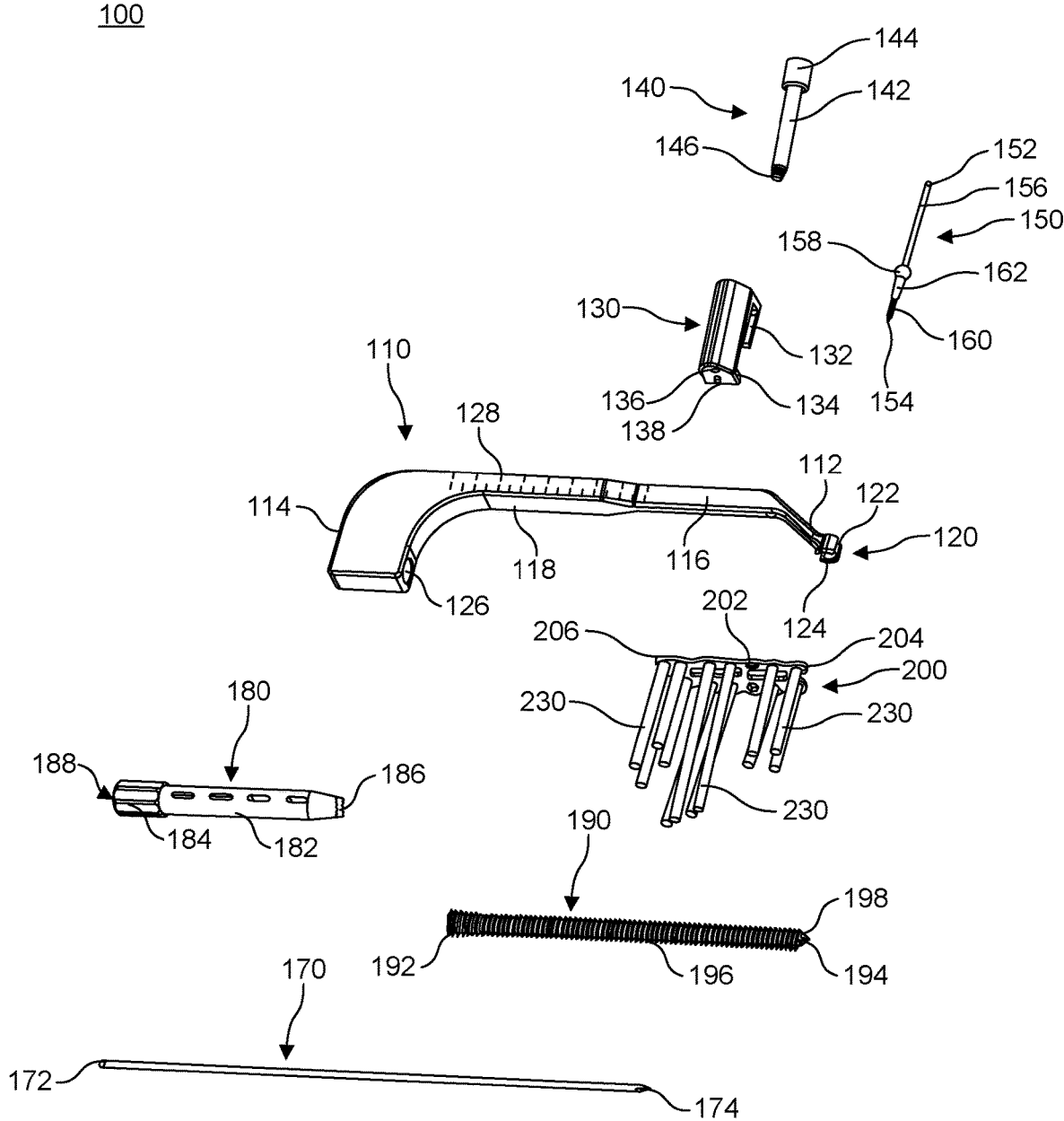
FIG. 8 is an exploded, bottom perspective view of the bone fixation system, bone plate and fasteners of FIG. 6, in accordance with an aspect of the present disclosure.
Figure 9:
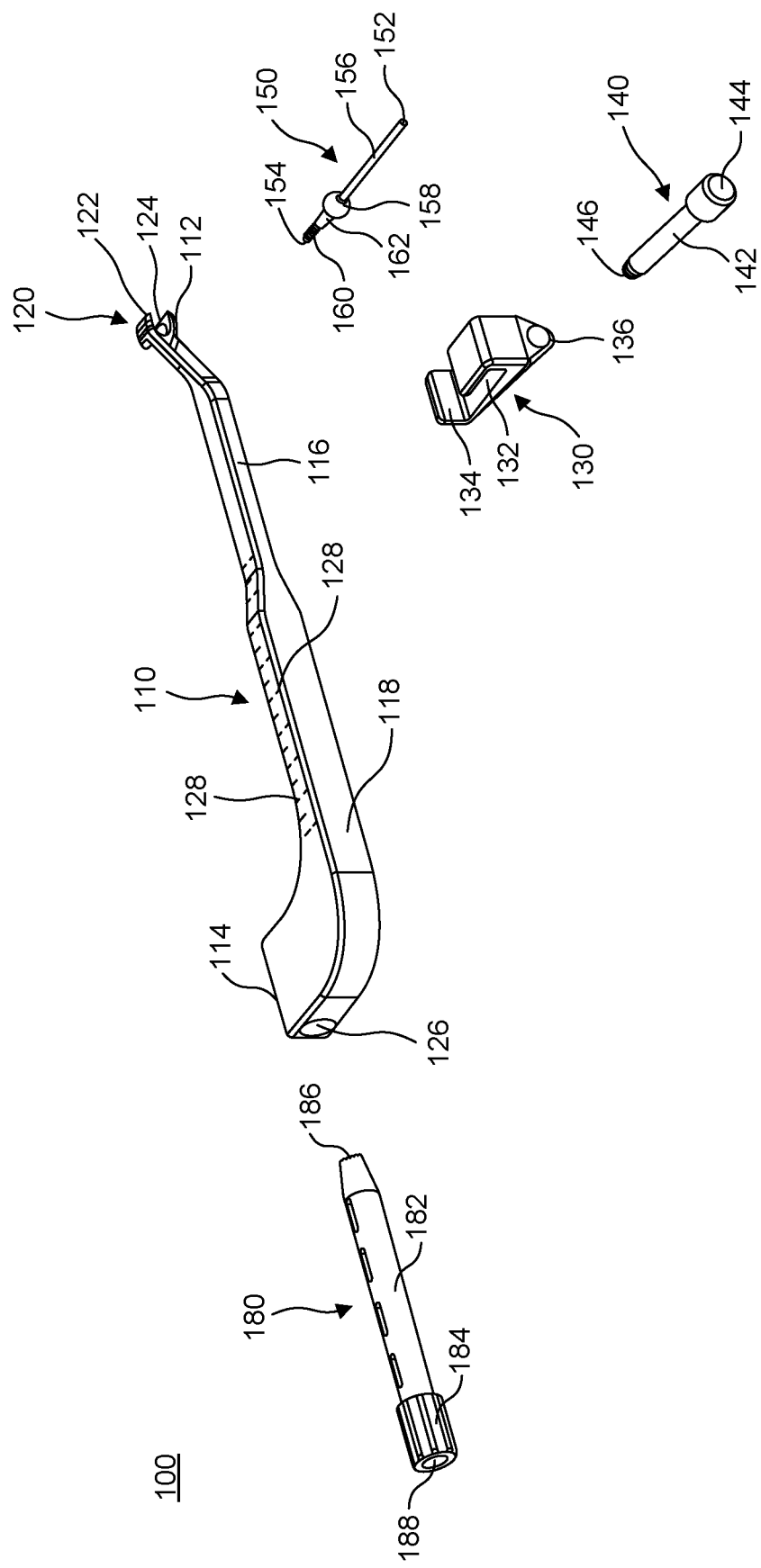
FIG. 9 is an exploded, top perspective view of a portion of the bone fixation system of FIG. 1, in accordance with an aspect of the present disclosure.
Figure 10:
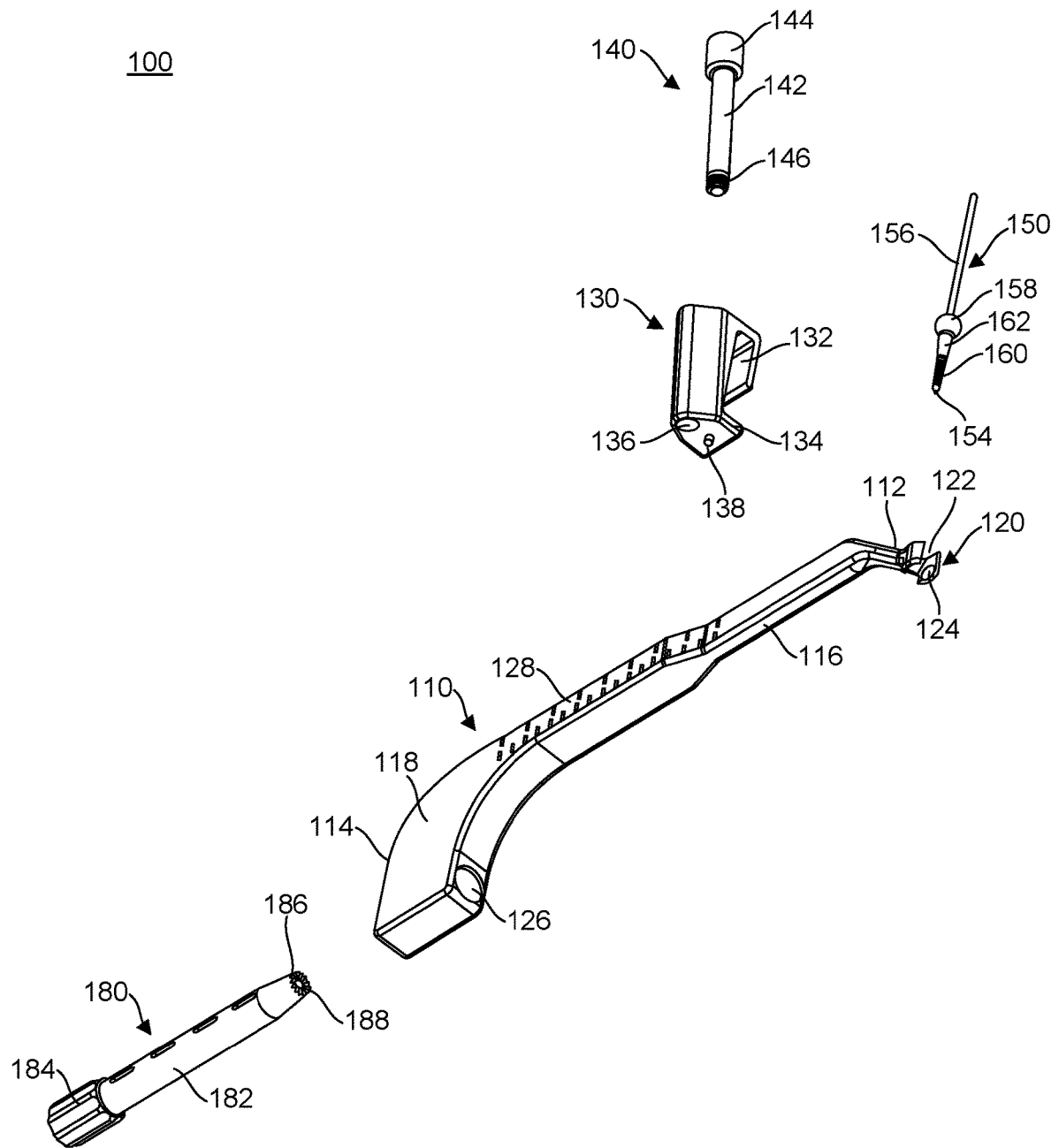
FIG. 10 is an exploded, bottom perspective view of a portion of the bone fixation system of FIG. 1, in accordance with an aspect of the present disclosure.

The alignment guide system 100 may also include a guide wire or k-wire 170, as shown in FIGS. 1-8. The guide wire 170 may include a first end 172 and a second end or insertion end 174, as shown in FIGS. 6-8.

As shown in FIGS. 6-10, the guide wire sleeve 180 of the alignment guide system 100 may include a body 182 with a first end 184 and a second end 186. The first end 184 may include a head portion or handle member. The second end 186 may have a tapered end terminating with a bone contacting surface that may be, for example, serrated or smooth. The guide wire sleeve 180 may also include a through hole or cannulation 188 extending through the body 182 from the first end 184 to the second end 186. The cannulation 188 may be, for example, sized and shaped to receive the guide wire 170.

The screw, beaming screw, solid screw or compression screw 190 may include a first end 192 and a second end 194, as shown in FIGS. 6-8. The head portion of the screw 190 positioned at the first end 192 may be, for example, tapered from the first end 192 to the threaded shaft portion 196. The beaming screw 190 may include threads 196 along at least a portion of the length. In addition, the beaming screw 190 may include a through hole or cannulation 198 extending from the first end 192 to the second end 194. The cannulation 198 may be sized and shaped to receive the guide wire 170 to allow for the beaming screw 190 to optionally be inserted over the guide wire 170. A drill (not shown) may optionally be inserted over the guide wire 170 to create a path for the screw 190 prior to inserting the screw 190 over the guide wire 170. Alternatively, the beaming screw 190 may be solid.

Figure 21:
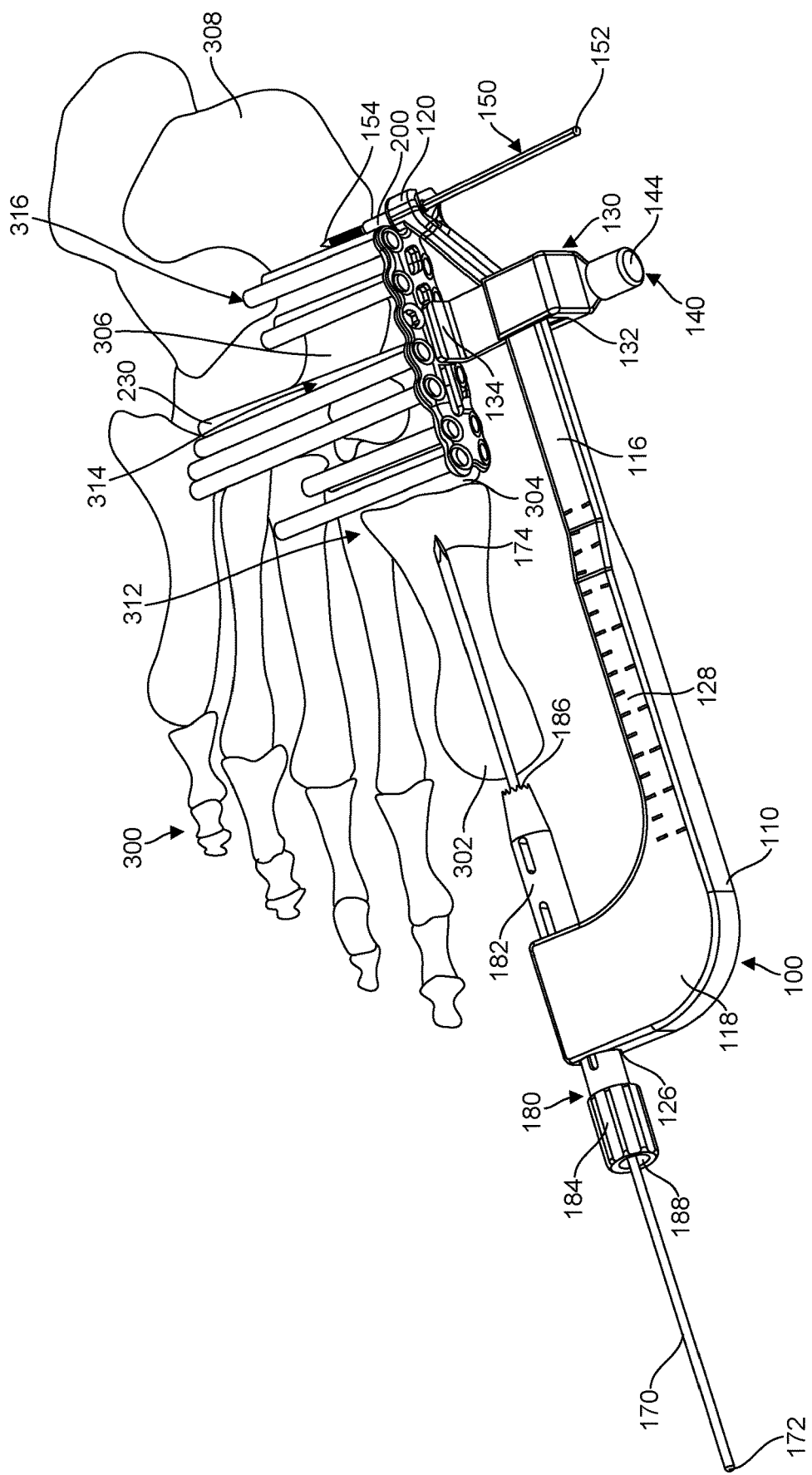
FIG. 21 is a dorsal perspective view of a portion of the bone fixation system of FIG. 1 and the bone plate and fasteners of FIG. 6, in accordance with an aspect of the present disclosure.
Figure 22:
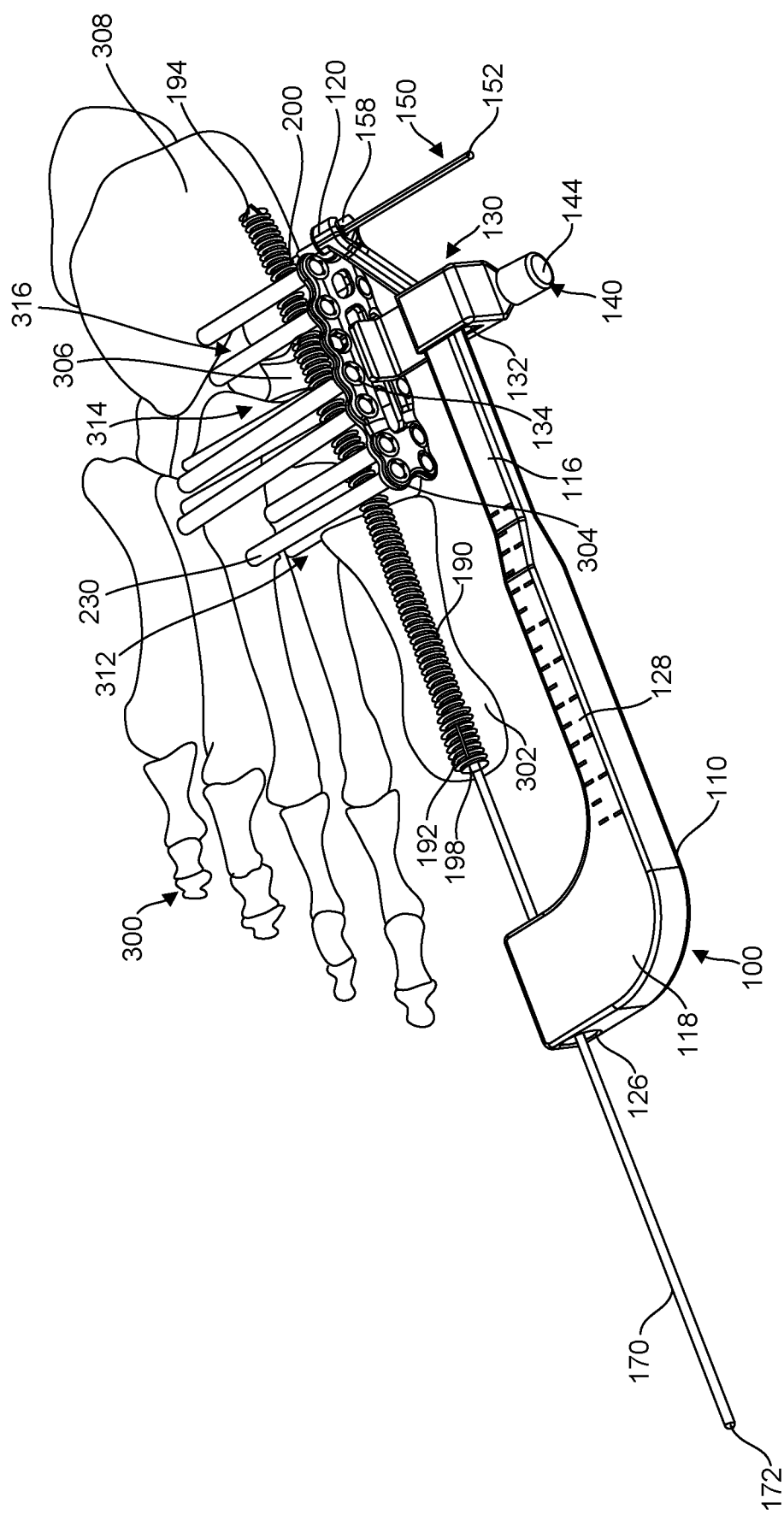
FIG. 22 is a dorsal perspective view of the bone fixation system of FIG. 1 and the bone plate and fasteners of FIG. 6, in accordance with an aspect of the present disclosure.
Figure 23:
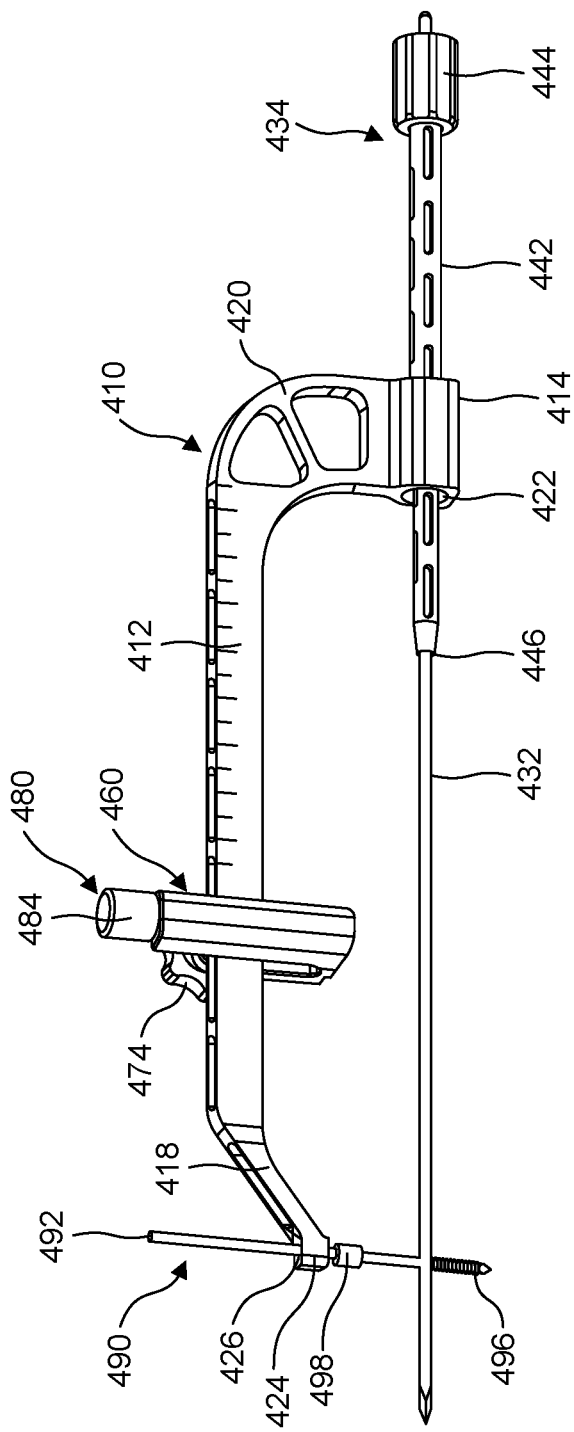
FIG. 23 is a first perspective, side view of a portion of another targeting guide system with a protector member, in accordance with an aspect of the present disclosure.
Figure 24:
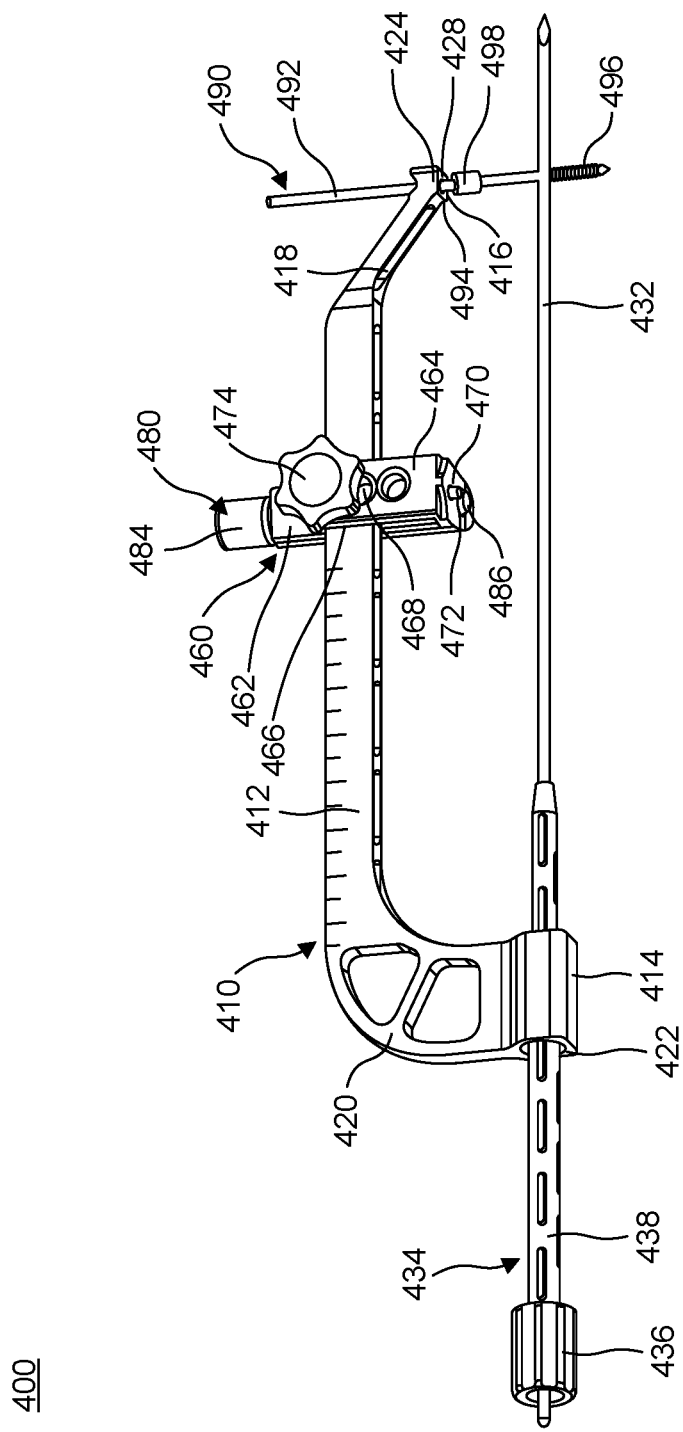
FIG. 24 is a second perspective, side view of the portion of the targeting guide system of FIG. 23, in accordance with an aspect of the present disclosure.
Figure 25:
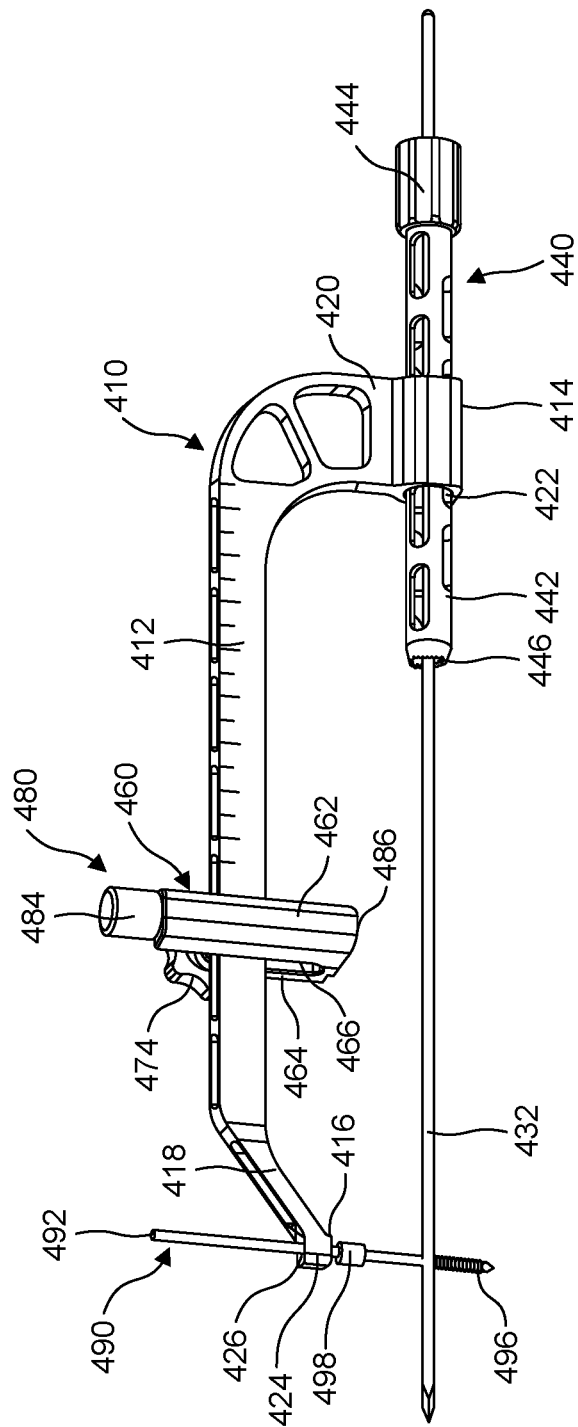
FIG. 25 is a first perspective, side view of the targeting guide system of FIG. 23 with a drill guide after removal of the protector member, in accordance with an aspect of the present disclosure.
Figure 26:
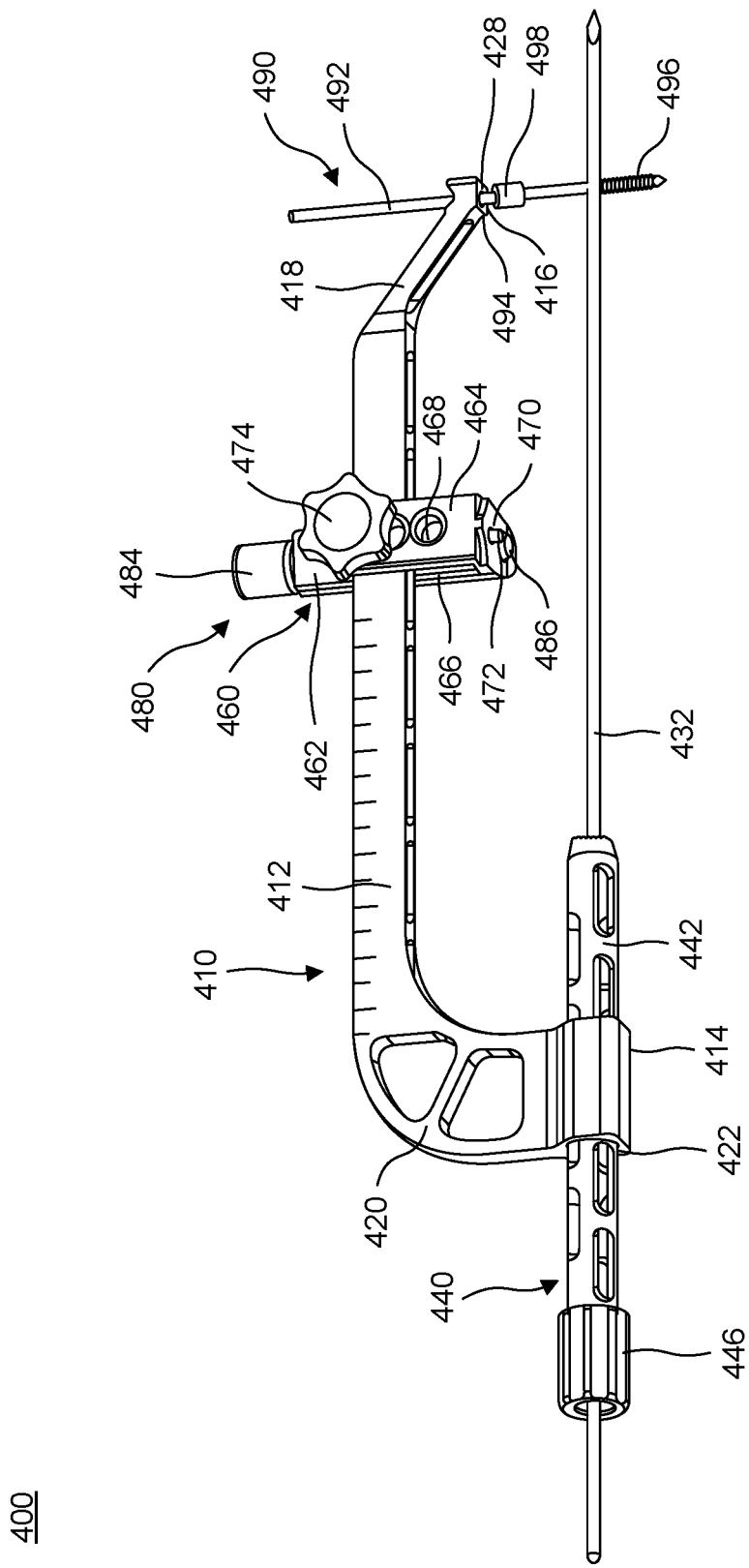
FIG. 26 is a second perspective, side view of the targeting guide system of FIG. 25, in accordance with an aspect of the present disclosure.
Figure 27:
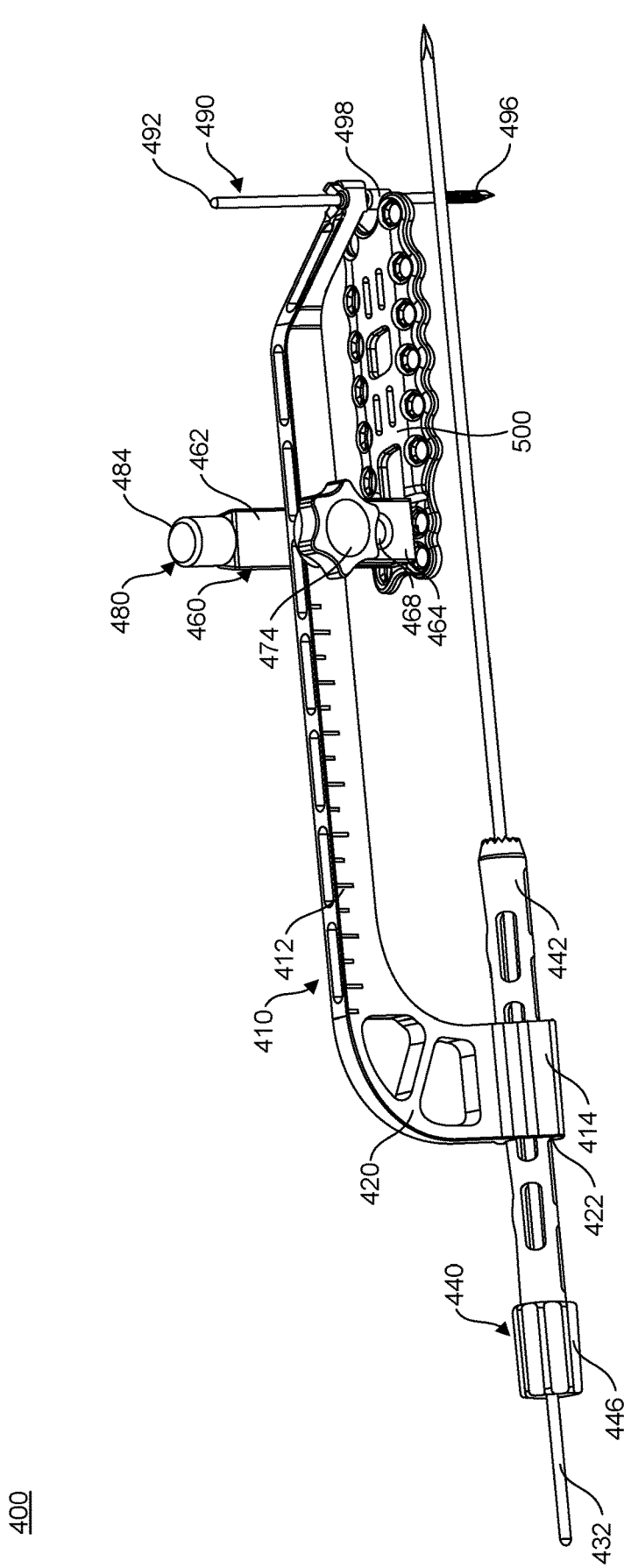
FIG. 27 is a perspective view of the targeting guide system of FIG. 25 with a bone plate attached, in accordance with an aspect of the present disclosure.
Figure 28:
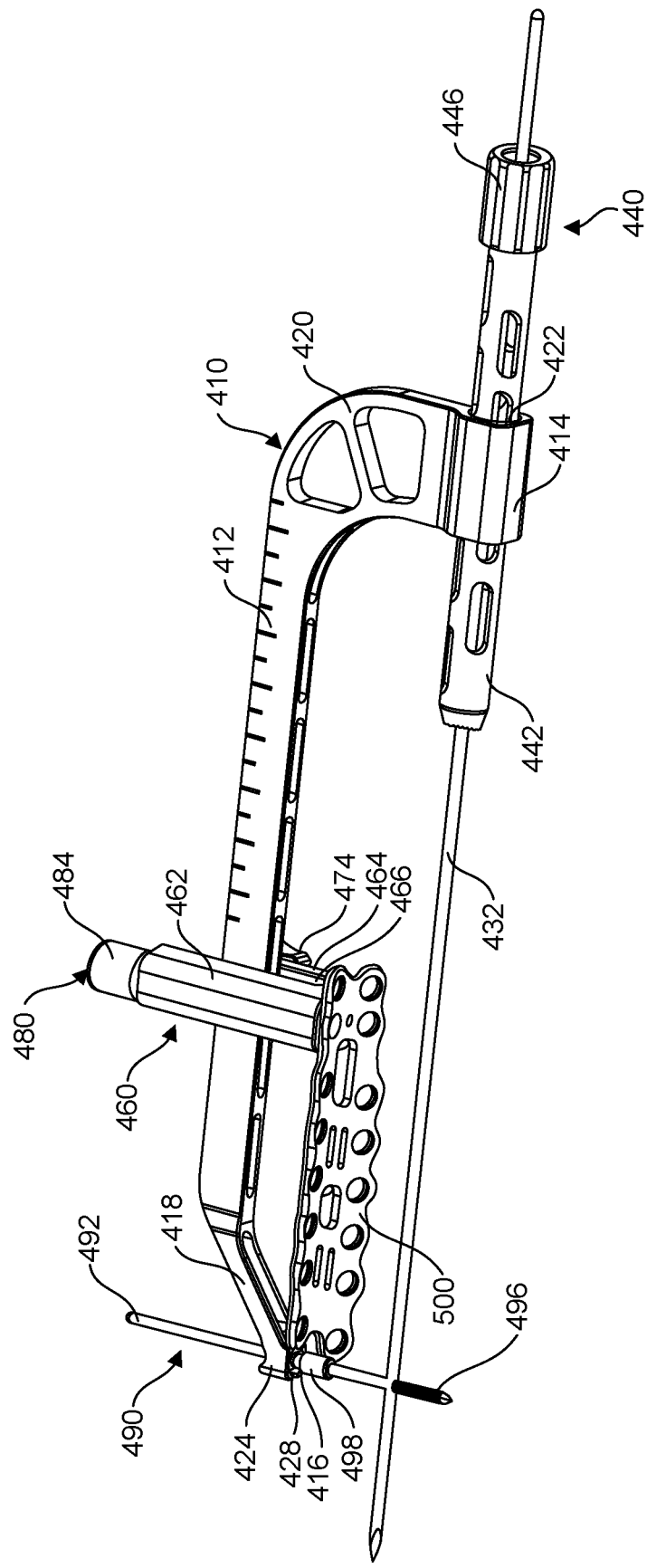
FIG. 28 is another perspective view of the targeting guide system of FIG. 27, in accordance with an aspect of the present disclosure.
Figure 29:
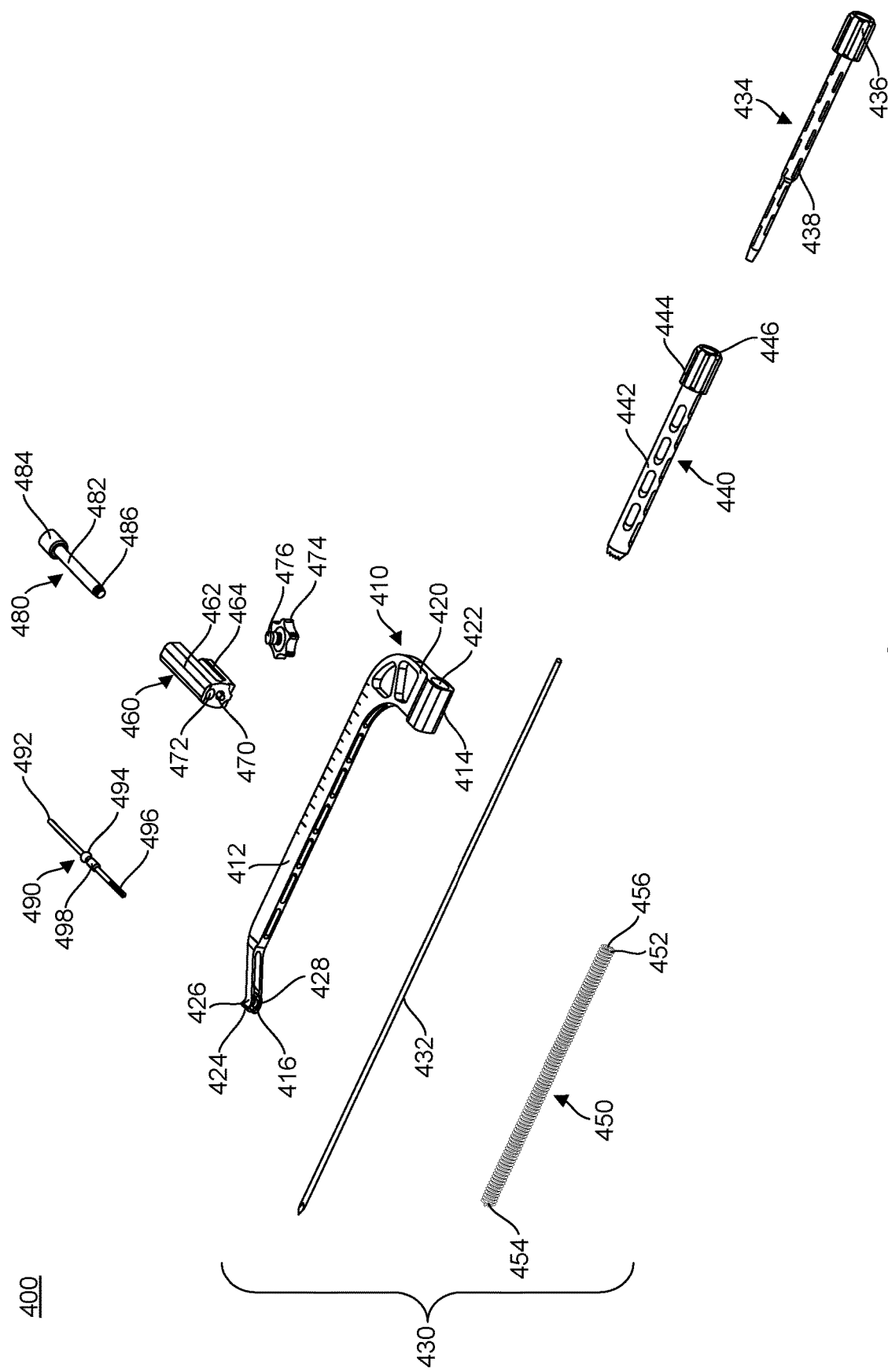
FIG. 29 is an exploded perspective view of the complete targeting guide system of FIG. 23, in accordance with an aspect of the present disclosure.
Figure 30:
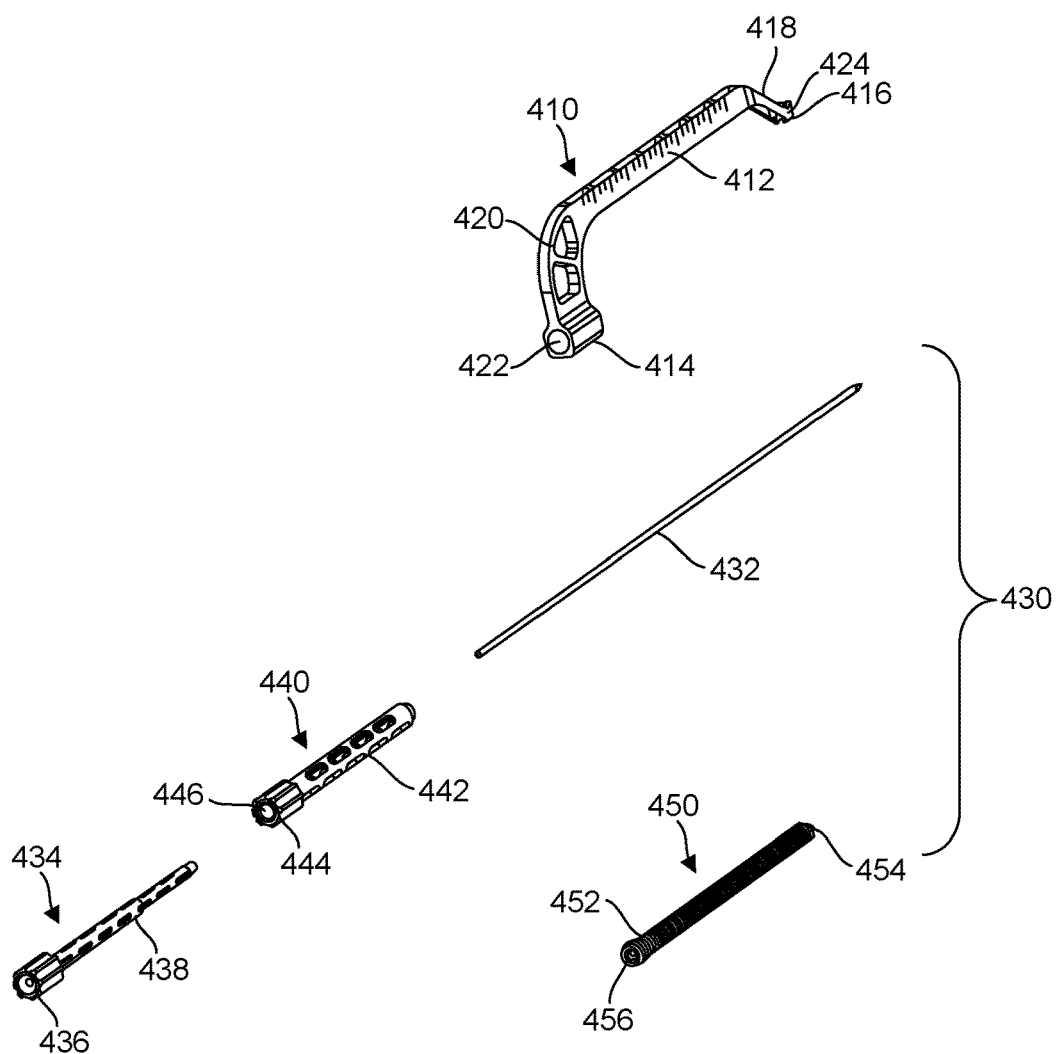
FIG. 30 is another exploded, perspective view of the targeting guide system of FIG. 29, in accordance with an aspect of the present disclosure.
Figure 31:
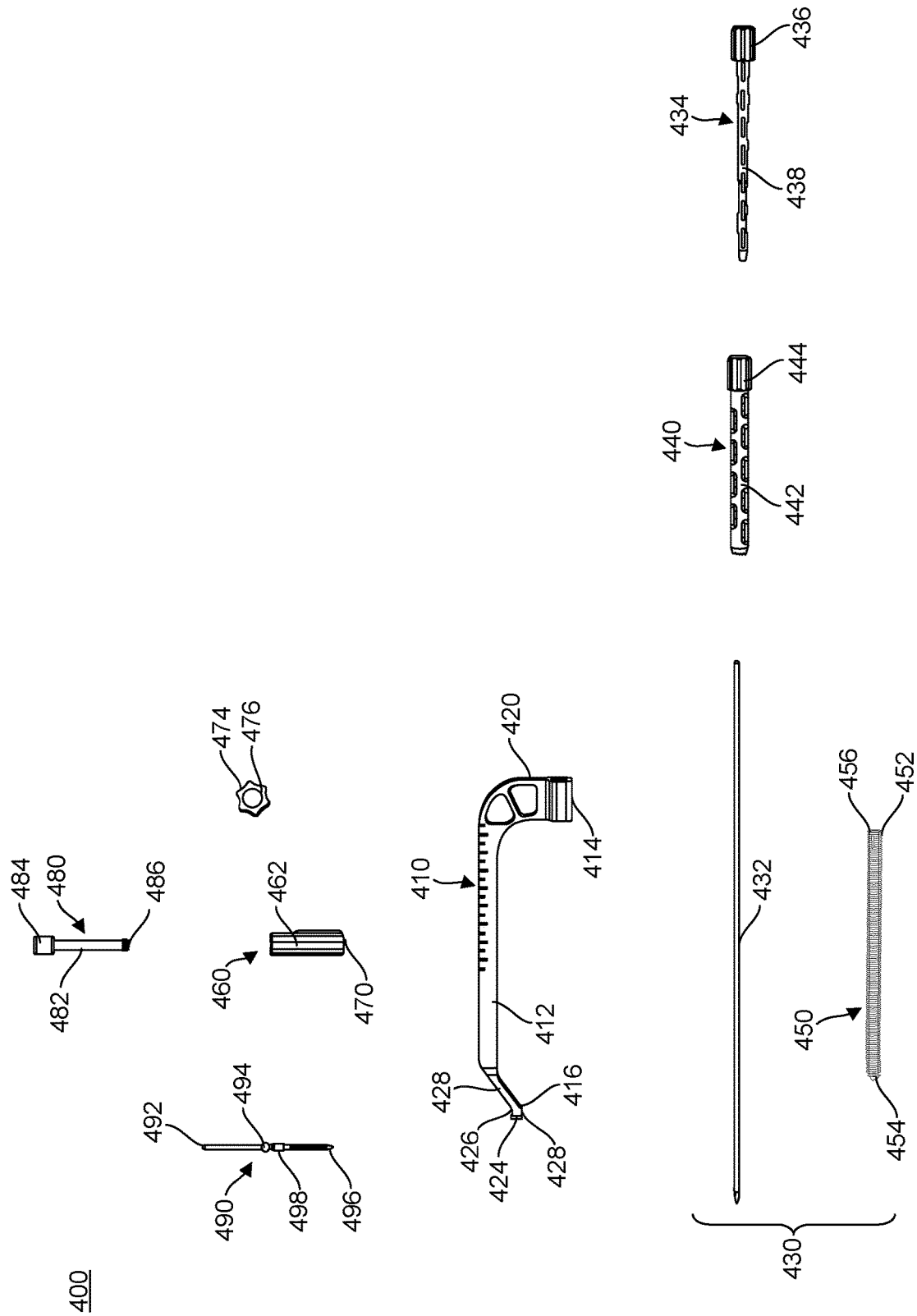
FIG. 31 is an exploded, first side view of the targeting guide system of FIG. 29, in accordance with an aspect of the present disclosure.
Figure 32:
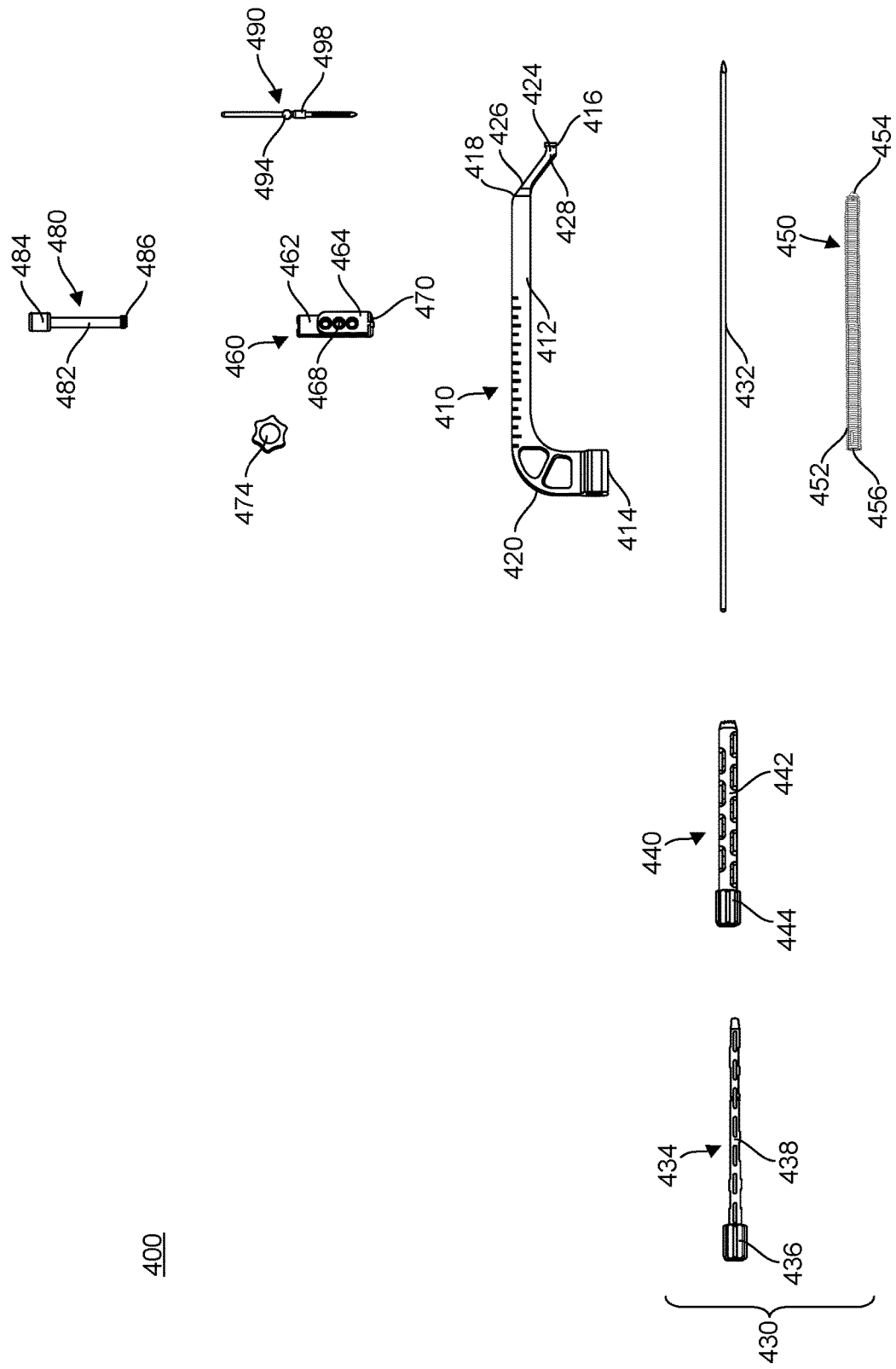
FIG. 32 is an exploded, second side view of the targeting guide system of FIG. 29, in accordance with an aspect of the present disclosure.

The bone fixation system 100 may also include a bone plate 200, as shown in FIGS. 6-8 and 11-16. The bone plate 200 may include a body 202 with a first end 204 and a second end 206. The body 202 may also include a plurality of lobes 208 extending away from the body 202, as shown in FIGS. 11 and 13-16. The body 202 may also include a plurality of screw holes or openings 210. Each of the plurality of screw holes 210 may be positioned in one of the plurality of lobes 208. The screw holes 210 are positioned to allow for bone fastener trajectories that form a longitudinal opening or space between the bone fasteners 230 inserted through the screw holes 210. The longitudinal opening or space is generally parallel to the body 202 of the bone plate 200. The bone fastener trajectories of the screw holes 210 are selected to provide the longitudinal opening for receiving a beaming screw 190 or to avoid interference or intersection with an already inserted beaming screw 190. The longitudinal opening may extend through, for example, at least one of the patient's joints. At least one of the plurality of screw holes 210 may be sized and shaped to receive the threaded portion 146 of the plate attachment member or set screw 140 to secure the plate 200 to the coupling member 130 of the alignment guide 110, as shown in FIGS. 21 and 22.

Figure 11:
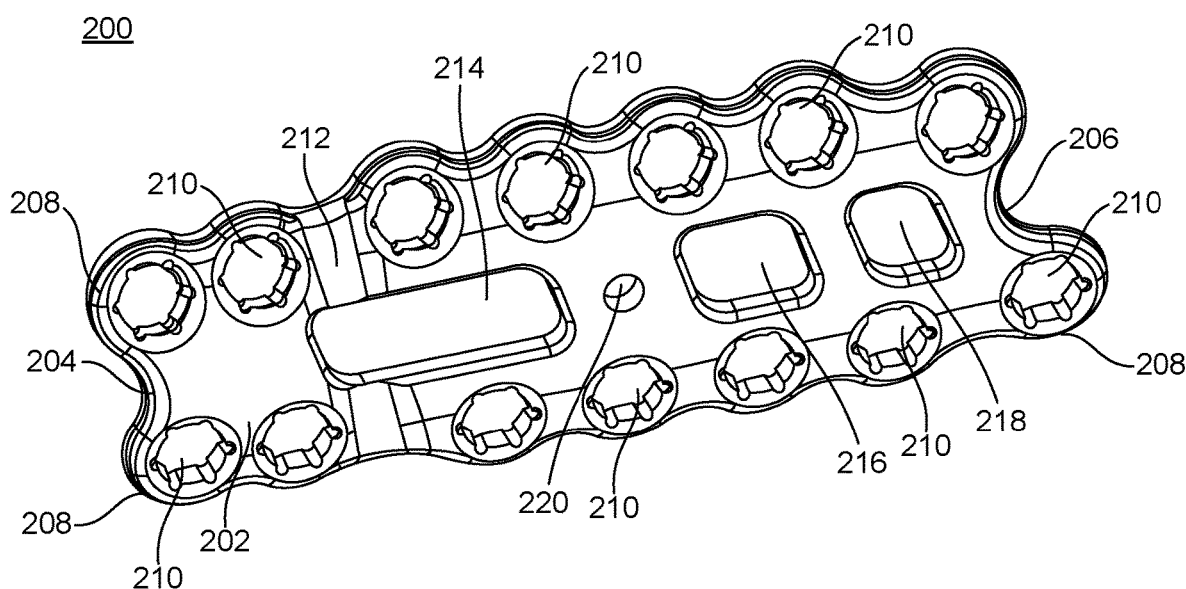
FIG. 11 is a top perspective view of the bone plate of FIG. 6, in accordance with an aspect of the present disclosure.
Figure 12:
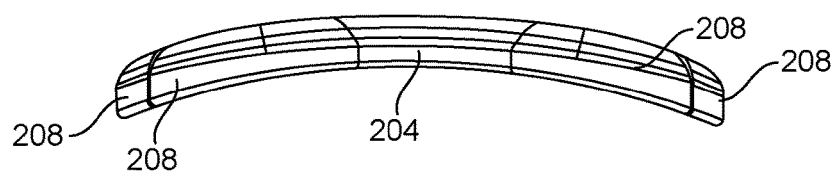
FIG. 12 is an end view of the bone plate of FIG. 6, in accordance with an aspect of the present disclosure.
Figure 13:
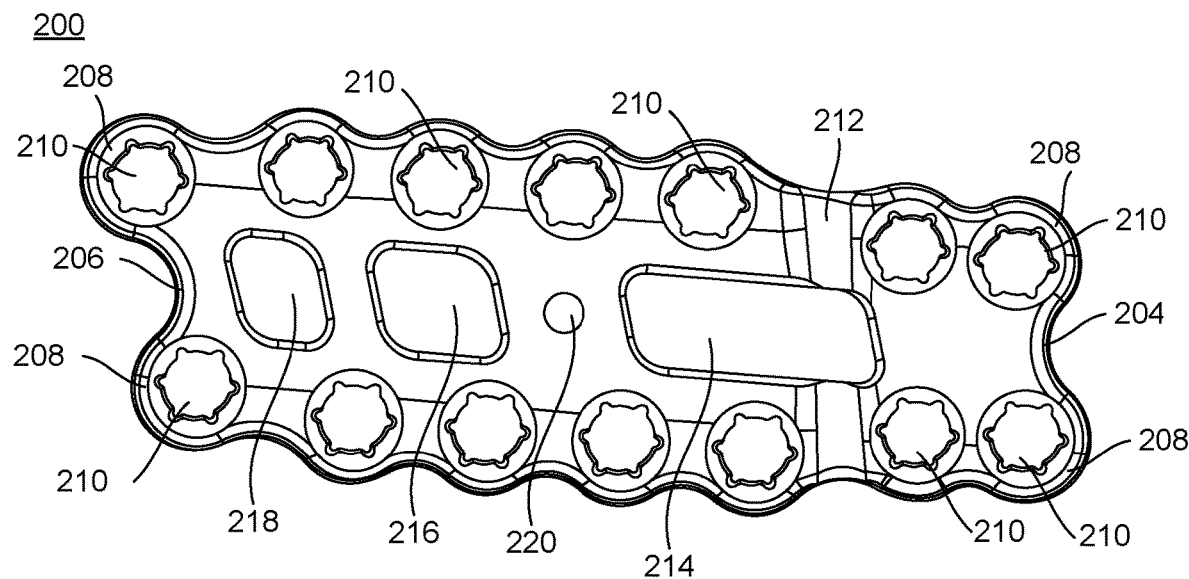
FIG. 13 is a top view of the bone plate of FIG. 6, in accordance with an aspect of the present disclosure.
Figure 14:
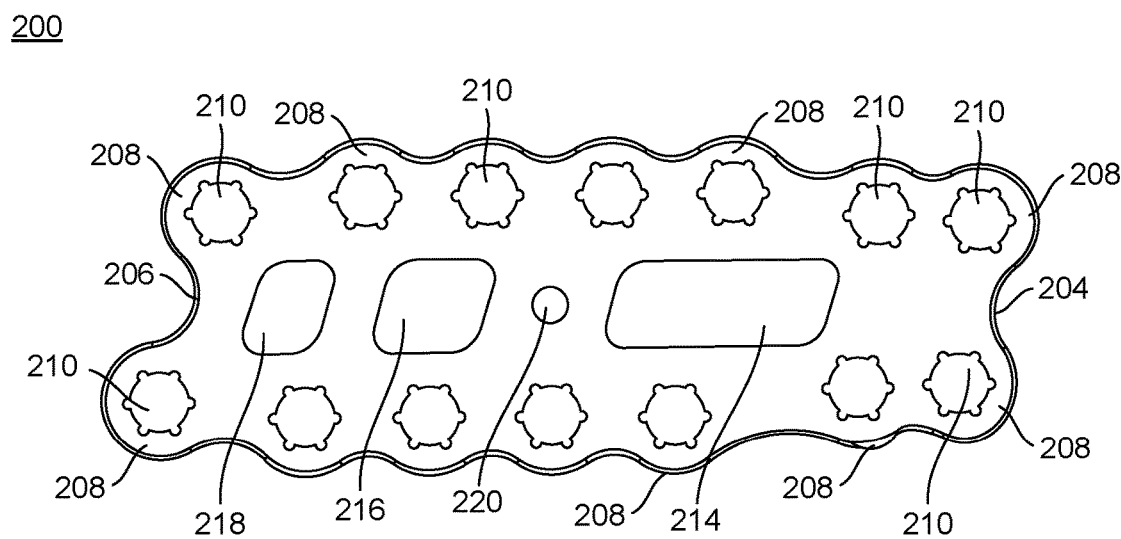
FIG. 14 is a back view of the bone plate of FIG. 6, in accordance with an aspect of the present disclosure.
Figure 15:
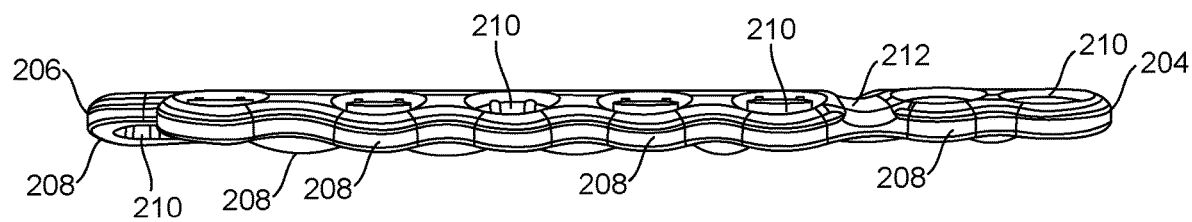
FIG. 15 is a first side view of the bone plate of FIG. 6, in accordance with an aspect of the present disclosure.
Figure 16:
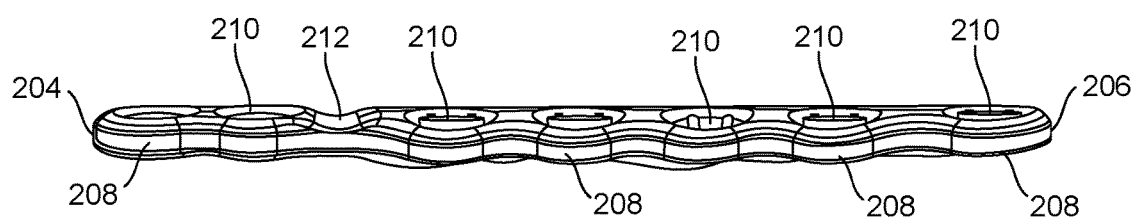
FIG. 16 is a second side view of the bone plate of FIG. 6, in accordance with an aspect of the present disclosure.

As shown in FIGS. 11, 13 and 14, the bone plate 200 may also include a first opening 214, a second opening 216, and a third opening 218 positioned along the longitudinal axis of the plate 200. The openings 214, 216, 218 may be, for example, sized and shaped to allow for visualization of the bones. The body 202 may also include an alignment hole 220 for receiving the alignment protrusion 138 of the coupling member 130. The alignment hole 220 may be positioned generally centered on the body 202. As shown, the alignment hole 220 may also be positioned between the first opening 214 and second opening 216 near a midpoint of the plate 200. Although not shown, the alignment hole 220 may alternatively be positioned anywhere along the plate to provide for coupling to the plate 200 with adequate visualization for the procedure. For example, the alignment hole 220 may be positioned between the opening 214 and the first end 204, between the openings 216, 218, or between the opening 218 and the second end 206. The third opening 218 may be positioned between the second opening 216 and the second end 206, as shown in FIGS. 11, 13 and 14. As shown in FIG. 12, the body 202 may be curved to match the curvature of the bones. The bone plate 200 may also include slots, as shown and described in greater detail below with reference to bone plate 500, positioned in the body 202 to allow for temporary fixation and compression of the bones being coupled to the plate 200.

Figure 17:
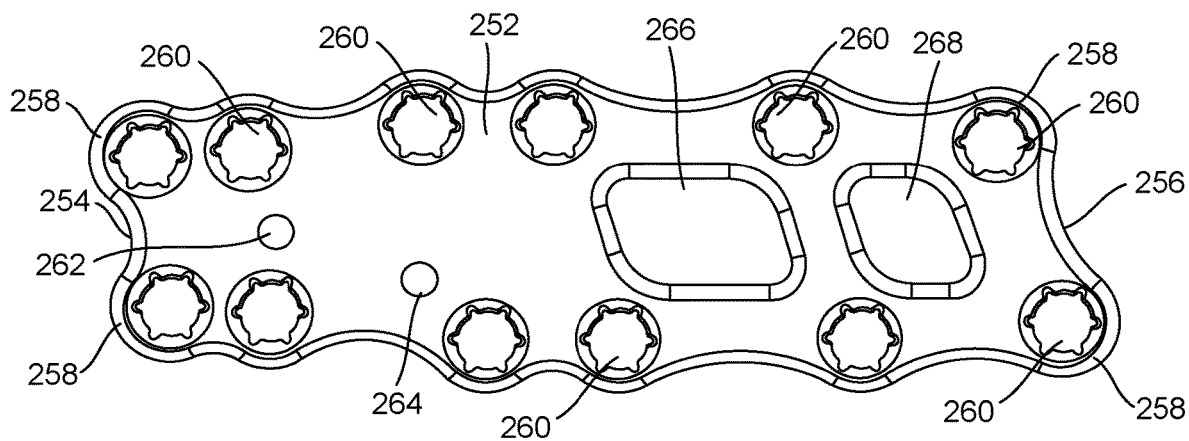
FIG. 17 is a top view of another bone plate, in accordance with an aspect of the present disclosure.
Figure 18:
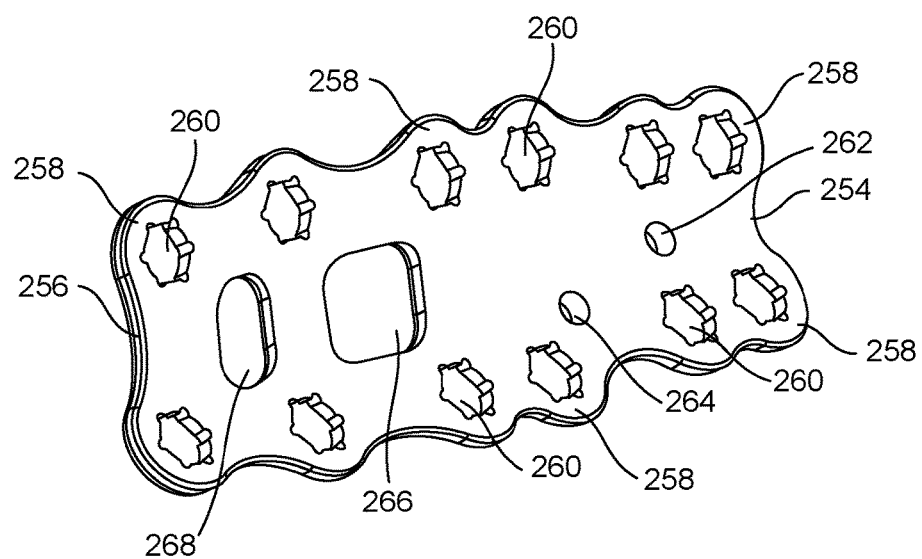
FIG. 18 is a bottom perspective view of the bone plate of FIG. 17, in accordance with an aspect of the present disclosure.

Referring now to FIGS. 17 and 18, another embodiment of a bone plate 250 is shown. The bone plate 250 may include a body 252 with a first end 254 and a second end 256. The body 252 may also include a plurality of lobes 258 extending away from the body 252, as shown in FIGS. 17-18. The body 252 may also include a plurality of screw holes or openings 260. Each of the plurality of screw holes 260 may be positioned in one of the plurality of lobes 258. At least one of the plurality of screw holes 260 may be sized and shaped to receive the threaded portion 146 of the plate attachment member or set screw 140 to secure the plate 250 to the coupling member 130 of the alignment guide 110.

With continued reference to FIGS. 17 and 18, the plate 250 also includes at least one alignment opening 262, 264 for receiving the alignment protrusion 138 of the coupling member 130. In the depicted embodiment, the plate 250 includes a first alignment opening 262 and a second alignment opening 264. The alignment opening 262, 264 may be positioned, for example, anywhere along the length of the plate 250. In addition, the plate 250 includes a first opening 266 and a second opening 268 for visualization of the bones during insertion.

The surgical method for using the bone fusion system 100 on a patient's foot 300 is shown in FIGS. 19-22. The method may use the bone fixation system 100 during an arthrodesis procedure, for example, for fusion of at least the first metatarsal 302 and the medial cuneiform 304 at the first tarsometatarsal joint 312. The bone fixation system 100 may also be used for fusion of, for example, the first tarsometatarsal joint 312 and naviculaocuneiform joint 314 to fuse the first metatarsal 302, the medial cuneiform 304 and the navicular 306 bones. It is also contemplated that the bone fixation system 100 may be used for fusion of, for example, the first metatarsal 302, the medial cuneiform 304, the navicular 306, and the talus 308 bones at the first tarsometatarsal joint 312, the naviculocuneiform joint 314 and the talonavicular joint 316, respectively. The bone fixation system 100 may also be used for treatment of Charcot neuroarthropathy where the breakdown of the medial column of the foot has occurred and restoration of the medial foot is necessary.

For example, the method may include making a skin incision to expose the first tarsometatarsal joint 312, the naviculocuneiform joint 314, the talonavicular joint 316, and the first metatarsophalangeal joint 310. Next, preparation of the joints 312, 314, 316 is performed by, for example, removing cartilage or performing osteotomies of the medial column joints 312, 314, 316. The joints may be prepared, for example, to obtain a plantigrade foot. After the joints are prepared, a guide wire 150, for example, a sphere wire may be placed into the talus 308. In procedures where fusion of the talonavicular joint 316 is not necessary, the sphere wire 150 may be placed in a more distal bone. The sphere wire 150 may be placed to position the tip 154 of the wire 150 or the threaded portion 160 of the wire 150 along the axis of the trajectory where a screw or beaming screw 190 will be inserted.

Figure 19:
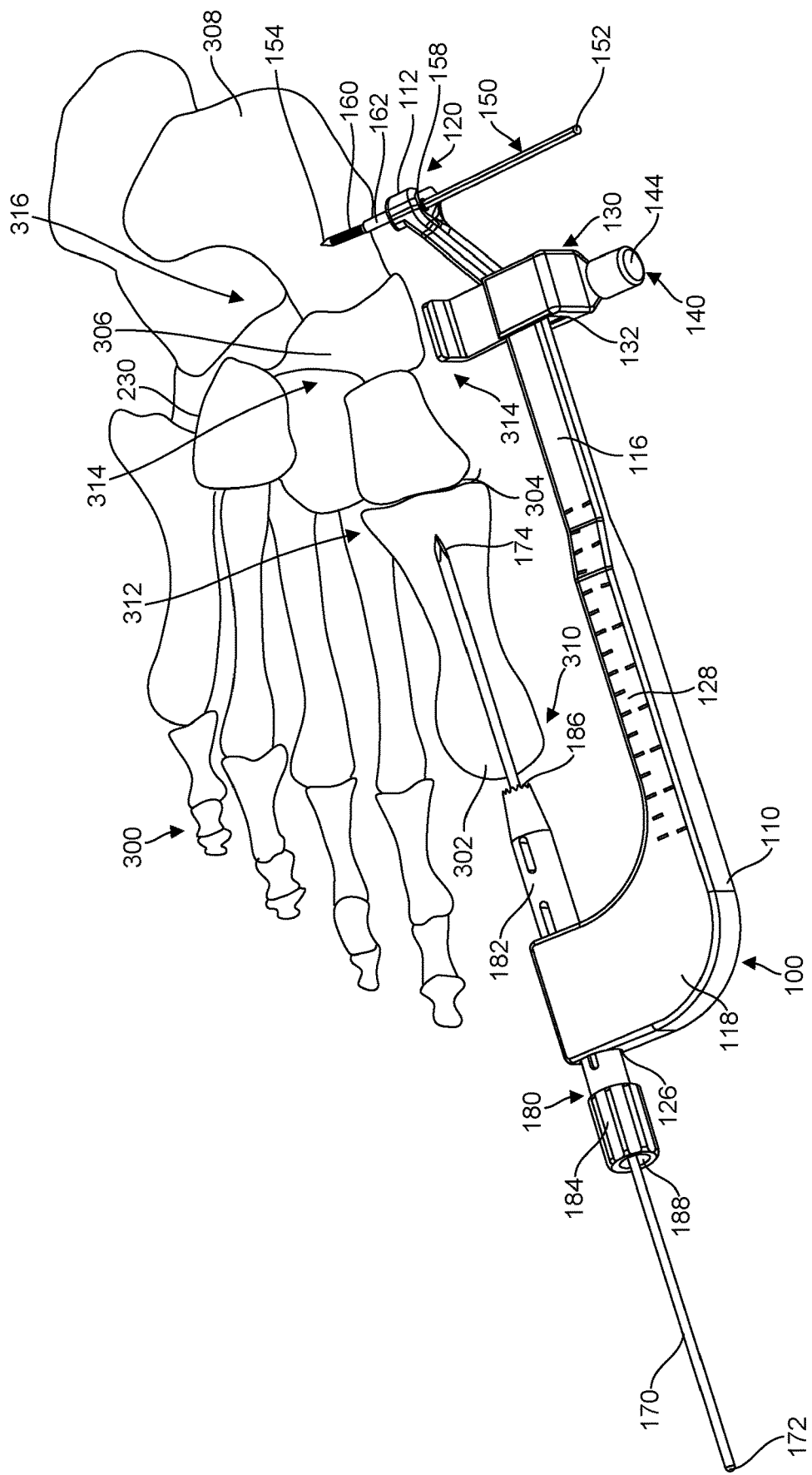
FIG. 19 is a dorsal perspective view of a portion of the bone fixation system of FIG. 1 positioned on a patient's foot, in accordance with an aspect of the present disclosure.

Next, an alignment guide 110 may be selected and coupled to the sphere wire 150. The pivot protrusion 158 of the sphere wire 150 may be, for example, inserted through the channel 122 and into engagement with the retaining member 124 inside of the pivoting head 120 of the alignment guide 110 to couple the sphere wire 150 to the alignment guide 110. The alignment guide 110 may be positioned to align the sleeve opening 126 with the central aspect of the first metatarsophalangeal joint 310. Then, a guide wire sleeve 180 may be inserted through the opening 126 in the distal end of the alignment guide 110. After the guide wire sleeve 180 is positioned, a guide wire 170 may be driven through the central aspect of the head of the first metatarsal 302, as shown in FIG. 19. The guide wire 170 may be driven proximally through the first metatarsal 302 and across, for example, the first tarsometatarsal joint 312, the naviculocuneiform joint 314 and the talonavicular joint 316. Once the guide wire 170 is inserted through the joints 312, 314, 316, the position of the guide wire 170 may be confirmed using fluoroscopy. If the guide wire 170 is in the desired position, the alignment guide 110 and the sphere wire 150 may be removed, for example, if only a beaming screw 190 is being inserted into the patient's foot 300.

Figure 20:
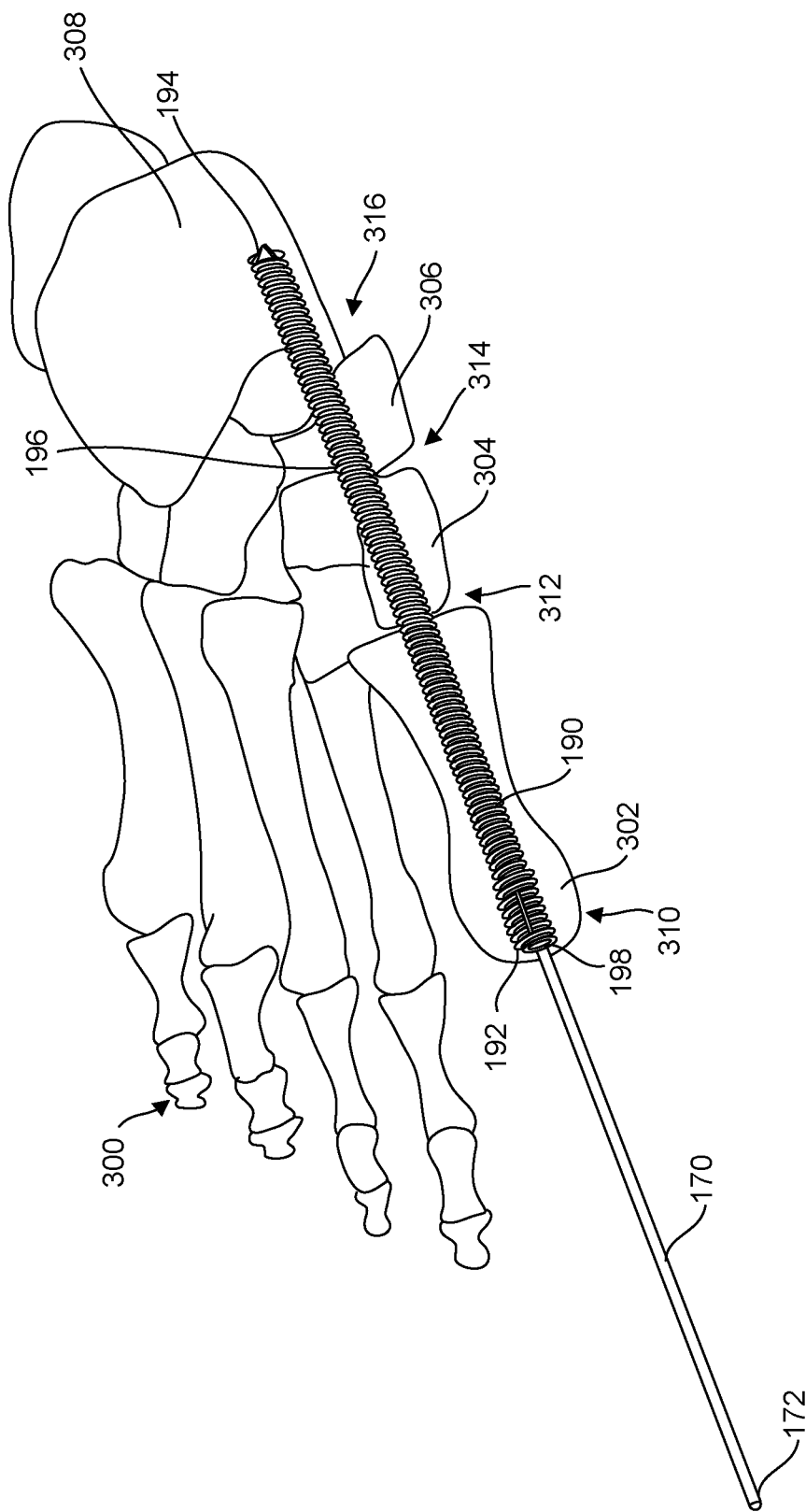
FIG. 20 is a dorsal perspective view of the guide wire and beaming screw of the bone fixation system of FIG. 1 positioned in a patient's foot, in accordance with an aspect of the present disclosure.

The beaming screw 190 may be inserted, as shown in FIG. 20, by drilling over the guide wire 170. After the drilling is complete, a cannulated screw, solid screw, or beaming screw 190 may be inserted into the first metatarsal 302 and across, for example, the first tarsometatarsal joint 312, the naviculocuneiform joint 314 and the talonavicular joint 316, if fusion of all three joints is desired. The screw 190 may be, for example, inserted over the guide wire 170 if the screw 190 is cannulated. Alternatively, if the screw 190 is solid, the guide wire 170 may be removed and then the screw 190 may be inserted through the opening in the patient's bones 302, 304, 306, 308. The screw 190 may be, for example, a headed or headless screw and a partially or fully threaded screw. The screw 190 may also have, for example, a tapered head portion with or without threads on the exterior surface.

In one embodiment, a bone plate 200 may be secured to the bones 302, 304, 306, 308, as shown in FIG. 22, for additional fixation, after the beaming screw 190 is inserted. Alternatively, the bone plate 200 may be secured to the bones after the guide wire 170 is placed but prior to beaming screw 190 placement. The plate 200 may be coupled to the coupling member 130 of the alignment guide 110 by aligning the opening 136 of the coupling member 130 with a screw hole 210 of the plate 200. The alignment protrusion 138 may be inserted into the alignment hole 220 in the plate 200 to assist with aligning the opening 136 with a screw hole 210. Next, a plate attachment member or set screw 140 may be inserted through the opening 136 and the threaded portion 146 may be screwed into a screw hole 210 of the plate 200. The channel 132 of the coupling member 130 may then be inserted over the first portion 116 of the alignment guide 110. Once the coupling member 130 is positioned on the first portion 116 of the alignment guide 110, the coupled plate 200 may be positioned on the patient's foot 300. The coupling member 130 enables translation along the alignment guide 110 to move the plate in a proximal-distal direction until a desired positioning is achieved on the patient's foot 300. The bone fixation system 100 also allows for rotation of the plate 200 in a frontal plane to allow for plate 200 fixation on a slightly more dorsal or plantar position depending on the patient's anatomy and desired correction. The coupled alignment guide 110 and plate 200 may rotate about the pivot protrusion 158 of the sphere wire 150. The translation and rotation of the plate 200 with respect to the patient's foot 300 allows for variations in the plate 200 positioning and for on-axis placement of the plate 200. Once the position of the plate is selected, bone plate screws 230 may be inserted through the screw holes 210 and the screw holes 210 may have trajectories to avoid contacting or interference with the beaming screw 190. In addition, the translation and rotation of the plate 200 allows for variations to the placement of the plate 200 before insertion of the bone plate screws 230 while still ensuring there is no contact or interference with the beaming screw 190.

In another embodiment, as shown in FIG. 21, after placement of the guide wire 170, the plate 200 may be positioned on the patient's foot, as described in greater detail above, which will not be described again here for brevity sake. Next, the plate 200 may be secured to the patient's bones 302, 304, 306, 308 by inserting bone fasteners 230 through the plurality of openings or screw holes 210 in the plate 200. The plate 200 may be secured to the patient's foot 300 prior to insertion of the beaming screw 190. The plurality of screw holes 210 may include insertion trajectories forming an opening or space between the plurality of bone fasteners 230 for insertion of the beaming screw 190. Once the plate 200 is attached to the patient's foot 300, then the guide wire sleeve 180 may be removed and a drill may be inserted over the guide wire 170 to drill an opening for a beaming screw 190. Next, a screw 190 may be inserted into the patient's foot 300. As the screw 190 is inserted, the screw 190 will avoid interference and/or intersection with the bone fasteners 230 and trajectory thereof. Once the screw 190 is positioned in the bones 302, 304, 306, 308, then the guide wire 170, spherical wire 150, and alignment guide 110 may be removed from the patient.

Finally, once the beaming screw 190 and/or plate 200 are secured to the patient's bones 302, 304, 306, 308, the arthrodesis procedure may be completed and the incision may be closed.

Referring now to FIGS. 23-43, another bone fixation system is shown. The bone fixation system may include a targeting guide assembly 400 and a bone plate 500. The targeting guide assembly 400 includes a guide arm 410, a target member 430, an implant holder 460, and a guide pin 490. The target member 430 is received within a first end of the guide arm 410. The implant holder 460 moveably engages the guide arm 410 and may, for example, slide along a top surface of a body 412 of the guide arm 410 to allow for location adjustability of a bone plate 500, as shown in FIGS. 34 and 35. The guide pin 490 rotatably couples to the second end of the guide arm 410. The implant holder 460 couples to a bone plate 500.

As shown in FIGS. 23-32, the guide arm 410 includes a body 412 connecting a first end 414 and a second end 416 of the guide arm 410. The first end 414 may, for example, include a wider portion 420 that includes arcuate sides that may attach the wider portion 420 in a generally perpendicular direction relative to the body 412. The wider portion 420 may also include a through hole 422 that is sized and shaped to receive the target member 430. The through hole 422 may be, for example, larger or smaller than as shown in FIGS. 23-32. The through hole 422 may extend through the wider portion 420 parallel to the body 412 allowing the target member 430 to extend parallel to the body 412 of the guide arm 410. The second end 416 may, for example, include an angled portion 418. The angled portion 418 extends in a downward angled direction from the body 412 to the second end 416. A housing element 424 may be positioned at the second end 416 and be configured or sized and shaped to receive the guide pin 490. The housing element 424 may include a top opening 426 and a bottom opening 428 forming an inner surface or cavity extending between the top opening 426 and the bottom opening 428. The housing element 424 may also include a channel extending from an exterior surface of the housing element 424 into the inner surface. The inner surface may be, for example, configured or sized and shaped to allow the guide pin 490 to pivot, rotate, or move in multiple planes. The top opening 426 may be sized to allow for insertion of a sphere 494 of the guide pin 490 into the housing element 424. The bottom opening 428 may be, for example, slightly smaller than the top opening 426 to capture or retain the guide pin 490 within the inner cavity of the housing element 424.

The target member 430 is shown in FIGS. 29-32 and includes a target pin 432, a protector member 434, a drill guide 440, and a threaded member or implant 450. The target pin 432 may be, for example, a guide wire, k-wire, pin, or the like elongated pin like structure or member for insertion through a joint. In the depicted embodiment the target pin 432 has a smooth outer surface with a point or sharped portion at one end.

The target pin 432 may be, for example, inserted from a distal to proximal direction through the cannulated opening of the protector member or guide wire targeting guide 434 when inserted into a bone pathway to secure the targeting guide in the surgical site and allow for the establishment of a target location proximally. The protector member 434 may include a knob 436 at a first end of a cylindrical portion 438. The protector member 434 may also include a through hole or cannulated opening extending through the protector member 434 along a longitudinal axis of the protector member 434. The protector member 434 may, for example, protect the surrounding soft tissue when the target pin 432 is inserted through the protector member 434 and into a patient's bones. The drill guide 440 may include a cylindrical portion 442 and a knob 444 positioned at a first end of the cylindrical portion 442. The cylindrical portion 442 of the drill guide 440 may have, for example, a larger diameter than the cylindrical portion 438 of the protector member 434. The drill guide 440 may also include a through hole or cannulated opening 446 extending along a longitudinal axis of the drill guide 440. The cannulated opening 446 of the drill guide 440 may be, for example, sized to receive the protector member 434. The drill guide 440 may, for example, protect the surrounding soft tissue when a drill is inserted through the cannulated opening 446 to drill an opening for inserting the threaded member 450. In one embodiment, the drill guide 440 may be inserted into the through hole 422 of the guide arm 410, the protector member 434 may be inserted into the cannulated opening 446, and the target pin 432 may be inserted through the protector member 434. In an alternative embodiment, the protector member 434 may be inserted into the through hole 422 of the guide arm 410, the target pin 432 may be inserted through the protector member 434, and then, the protector member 434 may be removed and the drill guide 440 inserted into the through hole 422 of the guide arm 410 over the target pin 432. The threaded member or implant 450 may include a head portion 452 at a first end of the threaded member 450 and cutting flutes 454 at a second end of the threaded member 450. The cutting flutes 454 may facilitate the insertion of the threaded member 450 into bones. In addition, the threaded member 450 may include a through hole or cannulated opening 456 extending through the threaded member 450 along a longitudinal axis. The through hole 456 may be configured or sized and shaped to receive the target pin 432. Alternatively, the threaded member 450 may be, for example, solid without a longitudinal opening. As shown, the threaded member 450 is threaded along the entire length, however, it is also contemplated that the threaded member 450 may be threaded along only a portion, for example, having partially or segmentally divided threads along the length.

The implant holder 460 may include a housing 462, a knob 474 and a locking member 480. The housing 462 may include an attachment arm 464 extending from and parallel to the housing 462 to form, for example, a U-shaped or hook like structure. The attachment arm 464 hooks under the bottom of the body 412 of the guide arm 410 to permit the sliding movement along the longitudinal axis of the body 412. A channel 466 is formed between the attachment arm 464 and the housing 462. The attachment arm 464 may also include at least one hole 468 extending through the attachment arm 464 from an exterior surface into the channel 466. The at least one hole 468 may be, for example, three holes. The implant holder 460 may also include an alignment post 470 extending away from a bottom surface of housing 462. The implant holder 460 may further include a through hole 472 extending through the housing 462 from a top surface to a bottom surface adjacent to the alignment post 470. The knob 474 may include an engagement protrusion 476 extending away from a back surface of the knob 474. The engagement protrusion 476 may be, for example, threaded to engage the at least one hole 468 to secure the implant holder 460 to the body 412 of the guide arm 410 at the desired position. The locking member 480 may include a shaft 482 with a knob 484 at a first end and a threaded portion 486 at a second end. The shaft 482 may be inserted through the through hole 472 of the housing 462 until the knob 484 contacts a top surface of the housing 462 and the threaded portion 486 extends past the bottom surface of the housing 462. The threaded portion 486 may engage a bone plate, such as bone plate 500, as described in greater detail below. The knob 474 may be rotated to insert the threaded portion 486 into the bone plate 500 and to remove the threaded portion 486 from the bone plate 500.

As shown in FIGS. 23-32, the guide pin 490 includes a shaft 492, a sphere 494, a tip 496, and a cylindrical protrusion 498. The sphere or spherical member 494 may be positioned between a first end and the tip 496. The tip 496 is threaded, however, it is also contemplated that the tip 496 may also have a smooth outer surface to facilitate insertion. The tip 496 is configured or sized and shaped to allow for the user to insert the guide pin 490 into a target bone either directly or through the skin. Once inserted into the target bone, the guide pin 490 may be secured to establish the target location for the threaded member 450. The sphere 494 is sized and shaped or configured to be inserted into the housing element 424 to allow for a full range of pivoting motions, as shown in FIGS. 23-28 and 33-35. The cylindrical protrusion 498 may be positioned adjacent to the sphere 494 between the sphere 494 and the tip 496.

Figure 40:
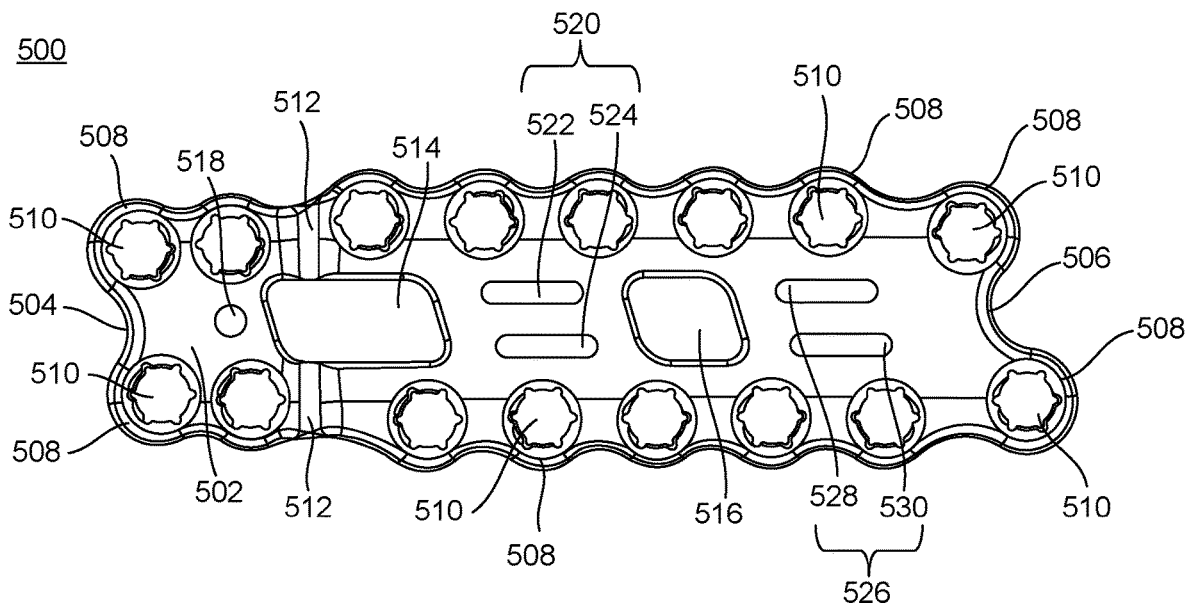
FIG. 40 is a top view of the bone plate of FIG. 27, in accordance with an aspect of the present disclosure.
Figure 41:
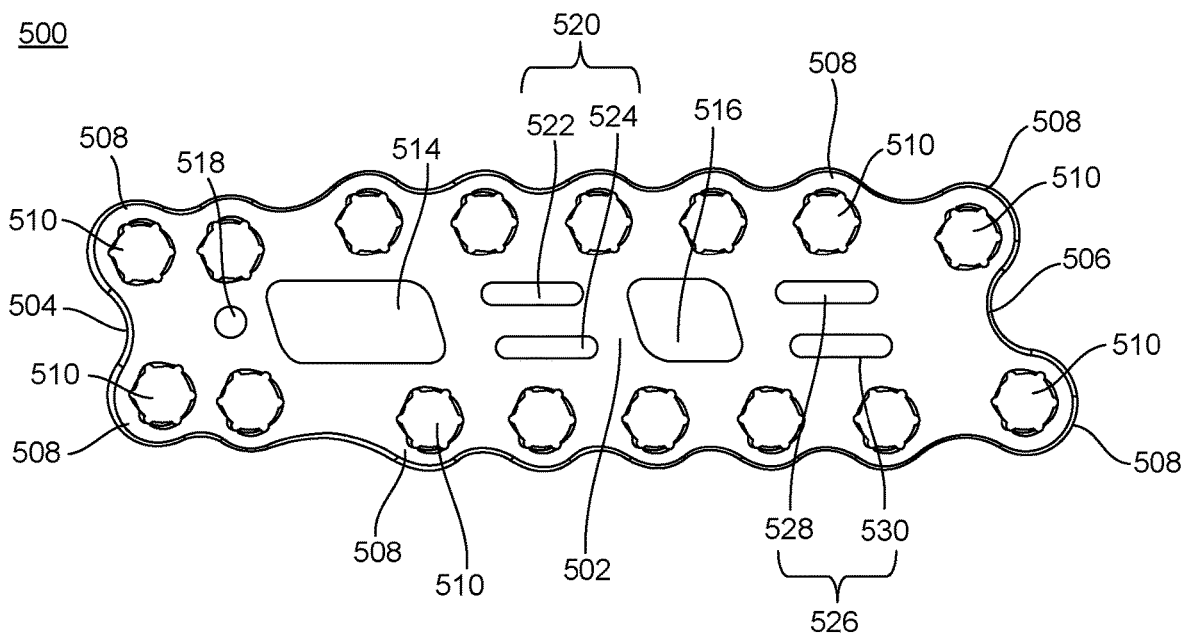
FIG. 41 is a bottom view of the bone plate of FIG. 27, in accordance with an aspect of the present disclosure.
Figure 42:
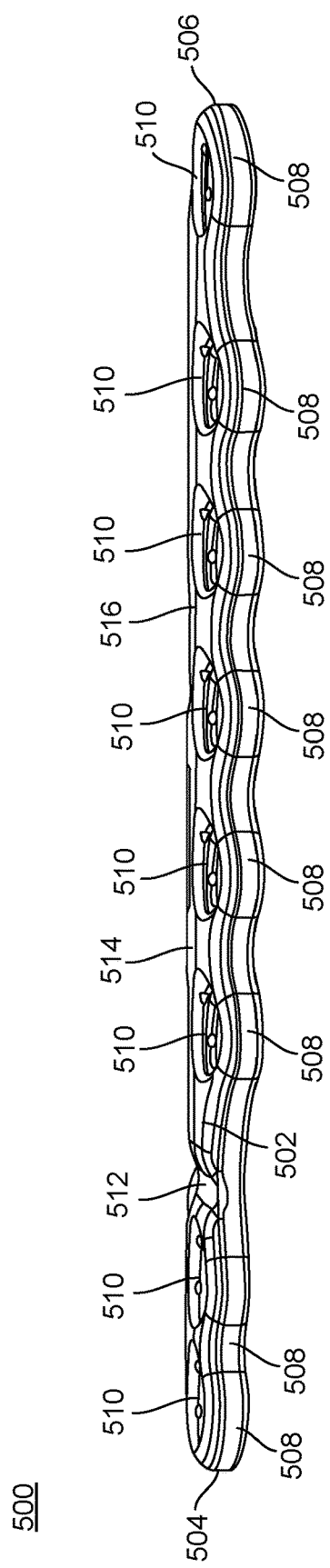
FIG. 42 is a first side view of the bone plate of FIG. 27, in accordance with an aspect of the present disclosure.
Figure 43:
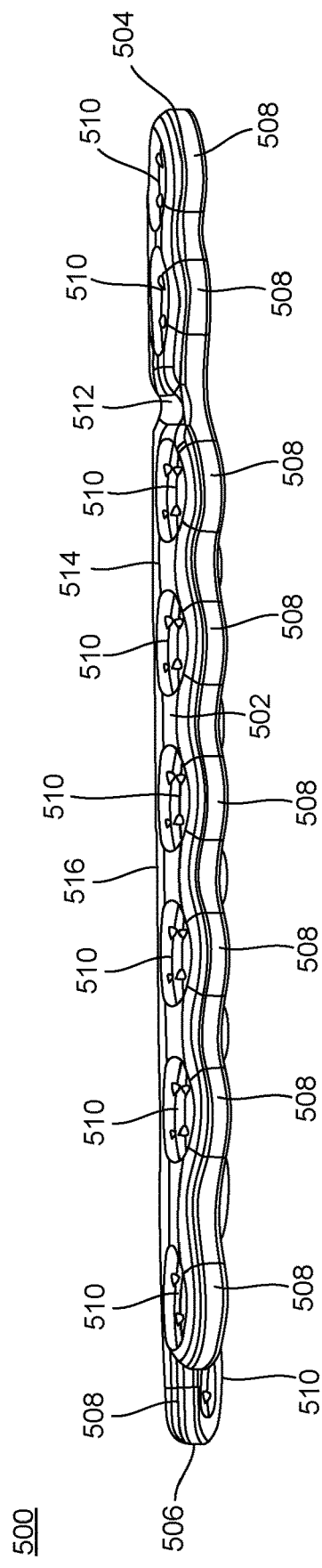
FIG. 43 is a second side view of the bone plate of FIG. 27, in accordance with an aspect of the present disclosure.

The targeting guide assembly 400 may be assembled by inserting the guide pin 490 into the housing element 424 of the guide arm 410. The protector member 434 may be inserted into the through hole 422 of the guide arm 410 to receive the target pin 432. In addition, the implant holder 460 may be aligned with the body 412 of the guide arm 410 and be secured in the desired position by engaging the engagement protrusion 476 with the body 412. The locking member 480 may be inserted into the opening 472 of the housing 462. Then, the alignment post 470 may be aligned with a corresponding alignment opening 518 in the bone plate 500, as shown in FIGS. 38, 40 and 41, and the threaded portion 486 of the locking member 480 may engage a corresponding screw hole 510 positioned adjacent to the alignment opening 518 in the bone plate 500. In addition, the protector member 434 may be removed and the drill guide 440 may be inserted into the through hole 422 of the guide arm 410 over the target pin 432.

As shown in FIGS. 38-43, the bone plate 500 may further include a body 502 with a first end 504 and a second end 506. The plate 500 may also include a plurality of lobes 508 positioned along the length of the plate 500. Each of the lobes 508 may include, for example, a screw hole or opening 510 for receiving a bone fastener, such as bone fasteners 540, as shown in FIGS. 34-37. The plate 500 may also include a groove 512 extending, for example, perpendicular to the longitudinal axis of the plate 500, as shown in FIGS. 38, 40, 42, and 43. The groove 512 may be positioned, for example, between two lobes 508 and two screw holes 510 on each side of the plate 500. The plate 500 may further include a first opening 514 and a second opening 516 positioned along the longitudinal axis of the plate 500. The openings 514, 516 may be, for example, sized and shaped to allow for visualization of the bones. The body 5020 may also include an alignment hole 518 for receiving the alignment post 470 of the implant holder 260. The alignment hole 518 may be, for example, positioned generally centered on the body 502 and between the first end 504 and the first opening 514. It is also contemplated that the alignment hole 518 may be, for example, positioned at alternative locations along the longitudinal axis of the plate 500 that allow for adequate visualization to perform the surgical procedure. In addition, the plate 500 may include a first pair of channels or slots 520 and a second pair of channels or slots 526. The first pair of channels 520 may include a first channel or slot 522 and a second channel or slot 524 positioned spaced apart from and adjacent to the first channel 522. The first pair of channels 520 may be, for example, positioned between the first opening 514 and the second opening 516. The second pair of channels 526 may include a third channel or slot 528 and a fourth channel or slot 530 positioned spaced apart from and adjacent to the third channel 528. The second pair of channels 526 may be, for example, positioned between the second opening 516 and the second end 506 of the plate 500. The channels or slots 522, 524, 528, 530 may, for example, allow for temporary fixation and compression of the bones being coupled to the plate 500. As shown in FIG. 39, the body 502 may be curved to match the curvature of the bones.

Figure 33:
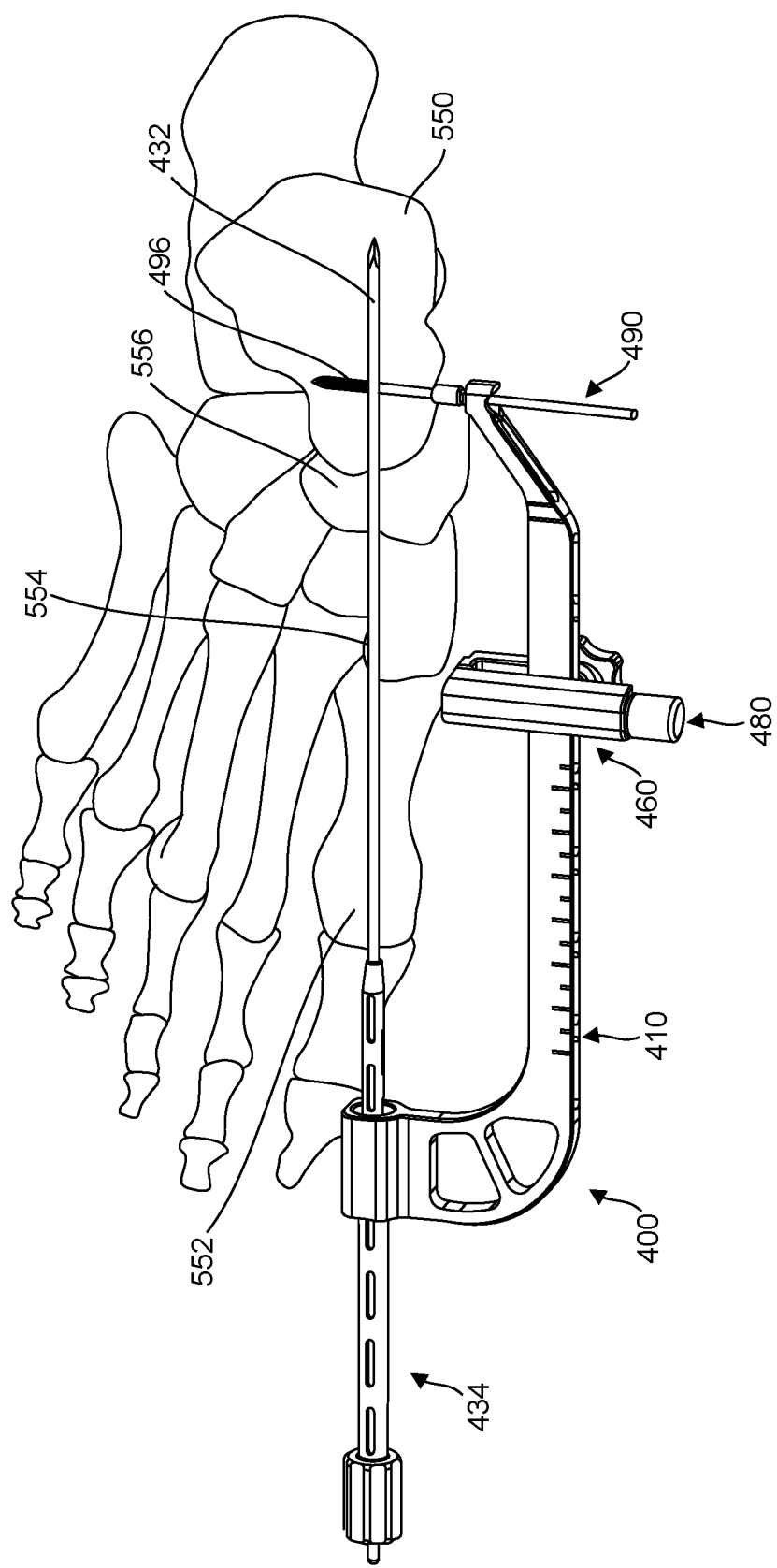
FIG. 33 is a dorsal view of the targeting guide system of FIG. 23 positioned on a foot, in accordance with an aspect of the present disclosure.
Figure 34:
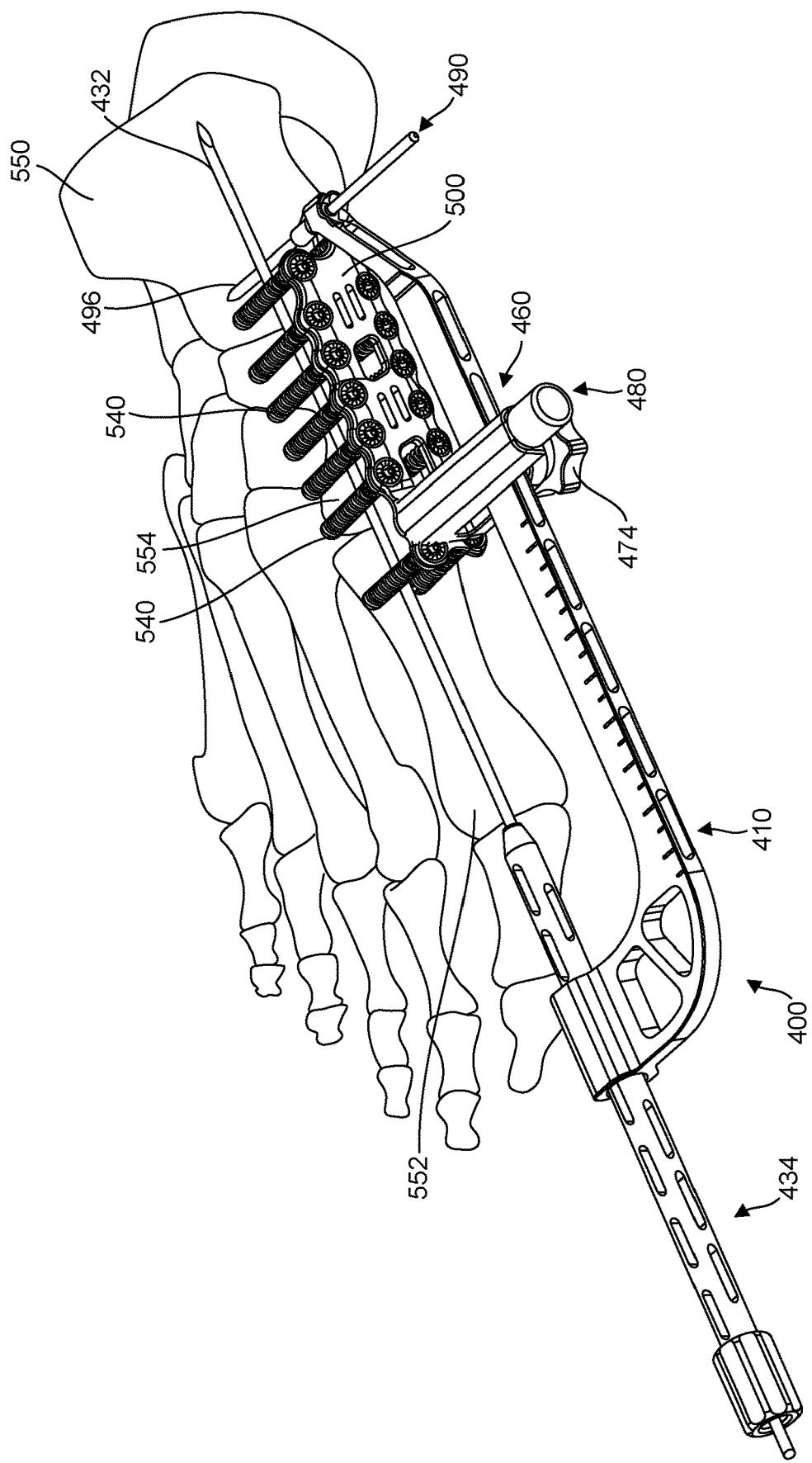
FIG. 34 is a perspective view of the foot and targeting guide system of FIG. 33 after a bone plate is secured to the foot with fasteners, in accordance with an aspect of the present disclosure.
Figure 35:
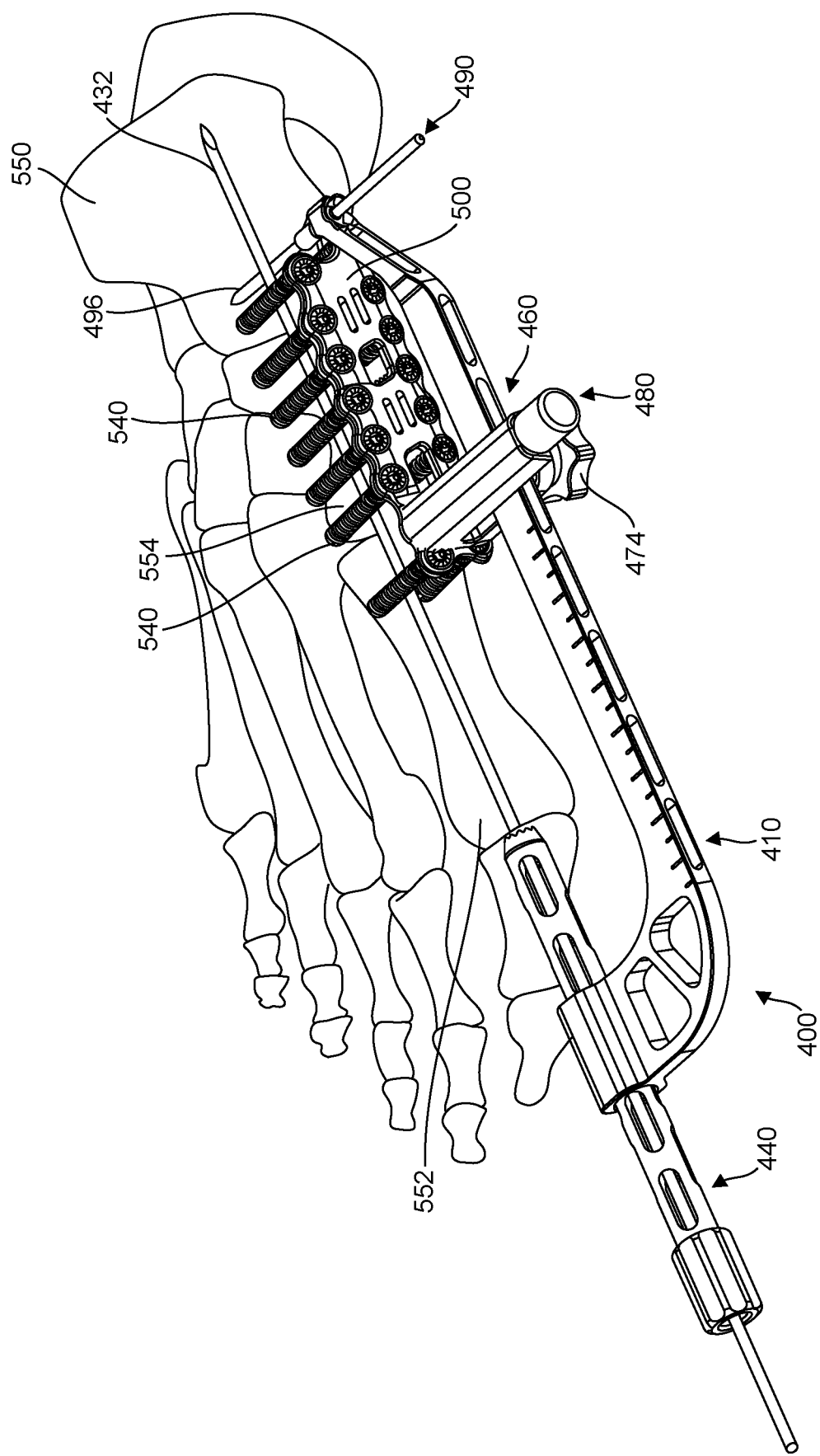
FIG. 35 is a perspective view of the foot and targeting guide system of FIG. 34 after removal of the protector member and insertion of the drill guide, in accordance with an aspect of the present disclosure.
Figure 36:
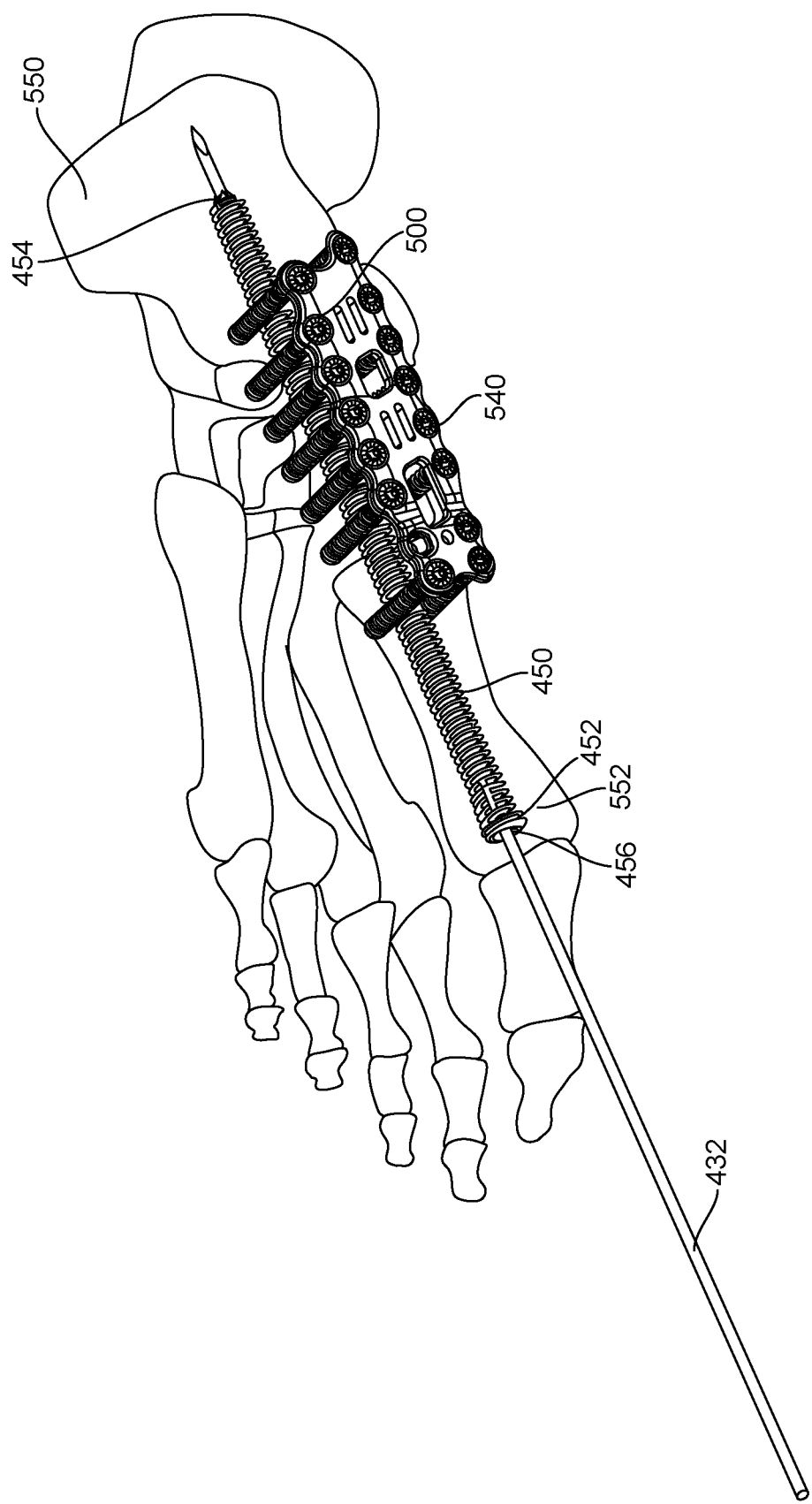
FIG. 36 is a perspective view of the foot of FIG. 35 after removal of the targeting guide system and insertion of a threaded member, in accordance with an aspect of the present disclosure.
Figure 37:
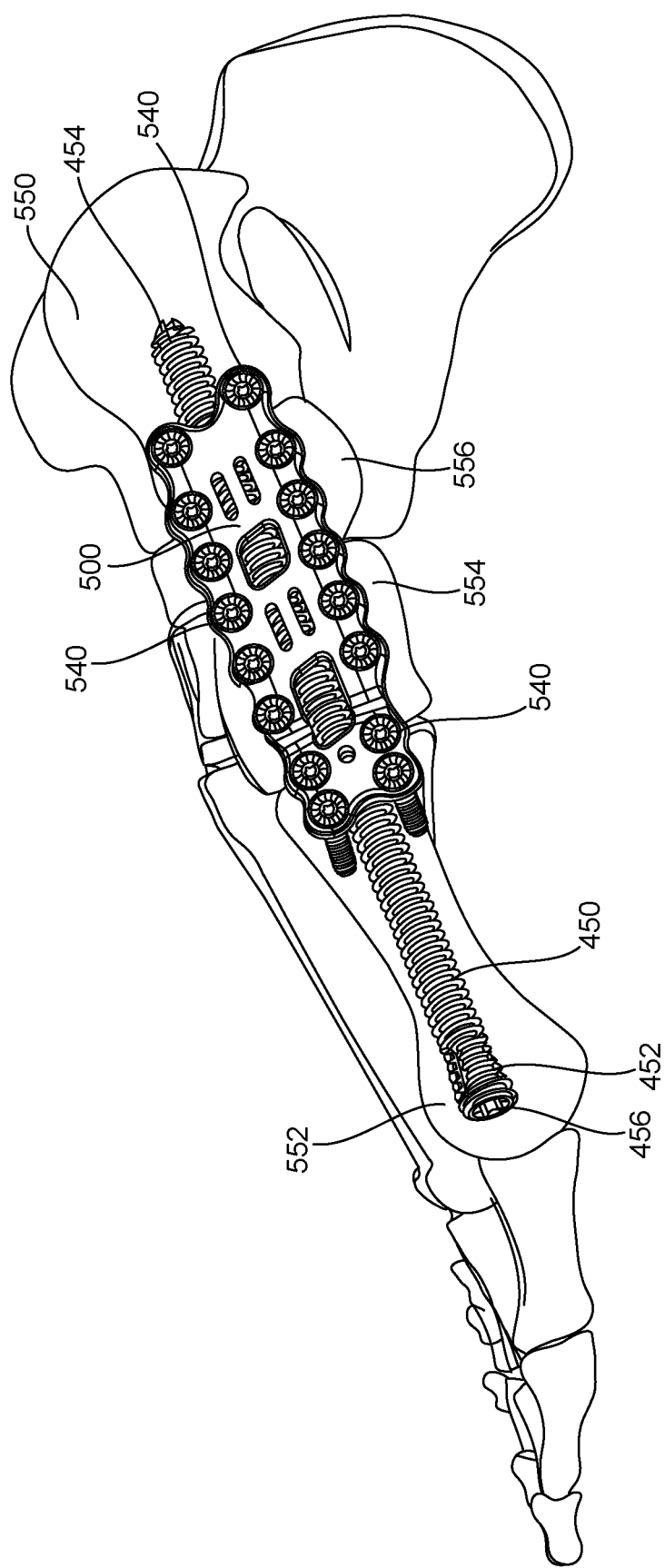
FIG. 37 is a side view of the foot of FIG. 36 after removal of the target pin, in accordance with an aspect of the present disclosure.

Referring now to FIGS. 33-37, a method for using the targeting guide assembly 400 to correct bone deformities is shown. The method may include, for example, performing an arthrodesis across at least one joint. The at least two bones of the at least one joint may be positioned in a desired final position and may be temporarily fixed. As shown in FIG. 33, the method may also include inserting a guide pin 490 into a first bone 550 to set the trajectory for the target pin 432 and the threaded member 450. Next, the housing element 424 of the guide arm 410 may be coupled to the sphere 494 of the guide pin 490. The guide arm 410 may be rotated about the sphere 494 to position the first end 414 of the guide arm 410 with respect to a second bone 552. Next, the protector member 434 may be inserted into the through hole 422 and a target pin 432 may be inserted through the protector member 434 and into at least one bone 552, 554, 556, 550. Alternatively, the drill guide 440 may be inserted into the through hole 422, the protector member 434 may be inserted into the cannulated opening 446 of the drill guide 400, and then the target pin 432 may be inserted through the protector member 434 and into at least one bone 552, 554, 556, 550. The trajectory of the target pin 432 will overlap or engage the guide pin 490. In one embodiment, the implant holder 460 may be coupled to the guide arm 410 before the guide arm 410 is coupled to the guide pin 490. Alternatively, the implant holder 460 may be coupled to the guide arm 410 after the target pin 432 is inserted into the bones 552, 554, 556, 550. The bone plate 500 may then be coupled to the implant holder 460 and aligned on the bones 552, 554, 556, 550, as shown in FIG. 34. It is also contemplated that the bone plate 500 may be coupled to the implant holder 460 prior to the guide arm 410 being coupled to the guide pin 490. Once the bone plate 500 is coupled to the implant holder 460, the position of the implant 500 may be adjusted along the length of the guide arm 410 to allow for implant positioning in a first plane, for example, the sagittal plane. The guide arm 410 may alternatively or in addition to adjustment along the length be rotated around the guide pin 490 to rotate the bone plate 500 in a second plane, for example, the frontal plane. Movement of the bone plate 500 in the two planes allows for fixation devices or bone screws 540 to be inserted with a trajectory to avoid contacting the target pin 432 and/or threaded member 450. The bone plate 500 may be secured to the bones 552, 554, 556, 550 with bone fasteners 540 inserted to avoid contacting the target pin 432 and the threaded member 450 when inserted. The bone fasteners or fixation devices 540 may be, for example, locking or non-locking fasteners. The method may then include removing the protector member 434 by sliding the protector member 434 out of the through hole 422 of the guide arm 410 over the target pin 432. As shown in FIG. 35, the drill guide 440 may then be inserted through the through hole 422 over the target pin 432 and positioned onto a bone 552. A cannulated drill may be used to drill over the target pin 432. The cannulated drill and drill guide 440 may then be removed from the guide arm 410 and the threaded member 450 may be inserted over the target pin 432 and into the bones 552, 554, 556, 550, as shown in FIG. 36. Although not shown, it is also contemplated that the bone plate 500 may be coupled to the bones 552, 554, 556, 550 after the threaded member 450 is inserted into the bones 552, 554, 556, 550. As also shown in FIG. 36, the guide arm 410 and guide pin 490 may be removed from the bones 552, 554, 556, 550. Finally, as shown in FIG. 37, the target pin 432 may be removed from the bones 552, 554, 556, 550 and the threaded member 450.

As may be recognized by those of ordinary skill in the art based on the teachings herein, numerous changes and modifications may be made to the above-described and other embodiments of the present disclosure without departing from the scope of the disclosure. The components of the instruments, guides, implants, plates, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, guides, implants, plates, and/or systems may include more or fewer components or features than the embodiments as described and illustrated herein. For example, the components and features of FIGS. 1-10 and FIGS. 23-32 may be used interchangeably and in alternative combinations as would be modified or altered by one of skill in the art. In addition, the components and features of FIGS. 11-16, FIGS. 17-18, and FIGS. 38-43 may be used interchangeably and in alternative combinations as would be modified or altered by one of skill in the art. Further, the steps of the surgical methods associated with FIGS. 19-20, FIGS. 21-22, and FIGS. 33-37 may be used interchangeably and in alternative combinations as would be modified or altered by one of skill in the art. Accordingly, this detailed description of the currently-described embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A bone plate, comprising:
a body including a first end, a second end, a top surface, and a bottom surface;
a plurality of lobes extending from the body;
a plurality of screw holes extending through the body between the top surface and the bottom surface, wherein each lobe of the plurality of lobes comprises a screw hole of the plurality of screw holes, wherein each screw hole extends through each lobe;
a groove inset into only the top surface of the bone plate and extending across the bone plate perpendicular to a longitudinal axis of the bone plate;
at least one alignment hole positioned along the body;
at least one opening positioned along the longitudinal axis of the bone plate and extending from the top surface through the bone plate to the bottom surface; and
at least one slot positioned along the longitudinal axis of the bone plate, wherein the at least one slot comprises:
a first pair of slots extending through the bone plate, wherein the first pair of slots comprises:
a first slot; and
a second slot positioned spaced apart from and parallel to the first slot, and wherein the first slot is offset along the longitudinal axis from the second slot; and
a second pair of slots extending through the bone plate and spaced apart from the first pair of slots, wherein the second pair of slots comprises:
a third slot; and
a fourth slot positioned spaced apart from and parallel to the third slot, and wherein the third slot is offset along the longitudinal axis from the fourth slot;
wherein the first pair of slots is positioned between a first opening of the at least one opening and a second opening of the at least one opening and the second pair of slots is positioned between the second opening and a second end of the bone plate.

2. The bone plate of claim 1, wherein the top surface is positioned substantially opposite the bone plate from the bottom surface.

3. The bone plate of claim 1, wherein the first end is positioned substantially opposite the bone plate from the second end.

4. The bone plate of claim 1, wherein the at least one opening comprises a first opening and a second opening.

5. The bone plate of claim 4, wherein the first opening and the second opening are the same size.

6. The bone plate of claim 4, wherein the first opening is larger than the second opening.

7. The bone plate of claim 4, wherein the second opening is larger than the first opening.

8. The bone plate of claim 4, wherein the first opening and the second opening are sized and positioned on the bone plate to facilitate viewing of an external surface of a bone through the first opening and the second opening.

9. The bone plate of claim 4, wherein the bone plate further comprises a third opening, wherein the third opening is larger than the first opening and the second opening.

10. The bone plate of claim 1, wherein the bone plate is curved in a transverse plane of the bone plate, wherein the curvature of the bone plate is configured to match a curvature of one or more bones.

11. The bone plate of claim 10, wherein the bone plate is curved such that a top surface of the bone plate has a convex geometry and a bottom surface of the bone plate has a concave geometry.

12. The bone plate of claim 1, wherein the at least one alignment hole is configured to receive one or more alignment components to facilitate positioning of the bone plate.

13. The bone plate of claim 1, wherein the at least one alignment hole is positioned generally centered on the body of the bone plate.

14. The bone plate of claim 1, wherein the at least one alignment hole is positioned generally at the first end of the bone plate.

15. The bone plate of claim 1, wherein the at least one alignment hole is a first alignment hole and a second alignment hole, wherein the first alignment hole and the second alignment hole are positioned adjacent the first end of the body of the bone plate.

16. A bone plate, comprising:
a body including a first end opposite a second end and a top surface opposite a bottom surface;
a plurality of lobes extending from the body;
a plurality of screw holes extending through the body between the top surface and the bottom surface, wherein each lobe of the plurality of lobes comprises a screw hole of the plurality of screw holes, wherein each screw hole extends through each lobe; and
a plurality of openings disposed along a longitudinal axis extending along a length of the body and extending from the top surface through the body to the bottom surface;
a curvature along a length of the plate such that the top surface comprises a first radius of curvature and the bottom surface comprises a second radius of curvature, wherein the first radius of curvature is greater than the second radius of curvature;
a groove inset into only the top surface extending across the body of the plate along the first radius of curvature; and
a plurality of slots positioned along the longitudinal axis of the body, wherein the plurality of slots comprises:
a first pair of slots extending through the body, wherein the first pair of slots comprises:
a first slot; and
a second slot positioned spaced apart from and parallel to the first slot, and wherein the first slot is offset along the longitudinal axis from the second slot; and
a second pair of slots extending through the body and spaced apart from the first pair of slots, wherein the second pair of slots comprises:
a third slot; and
a fourth slot positioned spaced apart from and parallel to the third slot, and wherein the third slot is offset along the longitudinal axis from the fourth slot;
wherein the first pair of slots is positioned between a first opening of the plurality of openings and a second opening of the plurality of openings and the second pair of slots is positioned between the second opening and a second end of the body.

* * * * *